(12) United States Patent
Sheffer et al.

(10) Patent No.: US 8,165,659 B2
(45) Date of Patent: Apr. 24, 2012

(54) MODELING METHOD AND APPARATUS FOR USE IN SURGICAL NAVIGATION

(76) Inventors: Garrett Sheffer, Hoboken, NJ (US); Byoungmoon You, Daejeon (KR)

(*) Notice: Subject to any disclaimer, the term of this patent is extended or adjusted under 35 U.S.C. 154(b) by 1155 days.

(21) Appl. No.: 11/689,711

(22) Filed: Mar. 22, 2007

(65) Prior Publication Data
US 2007/0270680 A1 Nov. 22, 2007

Related U.S. Application Data

(60) Provisional application No. 60/784,879, filed on Mar. 22, 2006.

(51) Int. Cl.
*A61B 5/05* (2006.01)
(52) U.S. Cl. ........ 600/427; 600/407; 600/424; 600/425; 600/426; 606/53
(58) Field of Classification Search .............. 606/53; 600/407, 424, 425, 426, 427
See application file for complete search history.

(56) References Cited

U.S. PATENT DOCUMENTS

| | | | |
|---|---|---|---|
| 5,016,639 A | 5/1991 | Allen | |
| 5,094,241 A | 3/1992 | Allen | |
| 5,097,839 A | 3/1992 | Allen | |
| 5,119,817 A | 6/1992 | Allen | |
| 5,142,930 A | 9/1992 | Allen et al. | |
| 5,222,499 A | 6/1993 | Allen et al. | |
| 5,230,338 A | 7/1993 | Allen et al. | |
| 5,389,101 A | 2/1995 | Heilbrun et al. | |
| 5,397,329 A | 3/1995 | Allen | |
| 5,603,318 A | 2/1997 | Heilbrun et al. | |
| 5,682,886 A | 11/1997 | Delp et al. | |
| 5,682,890 A | 11/1997 | Kormos et al. | |
| 5,772,594 A | 6/1998 | Barrick | |
| 5,836,954 A | 11/1998 | Heilbrun et al. | |
| 5,871,018 A | 2/1999 | Delp et al. | |
| 5,902,239 A | 5/1999 | Buurman | |
| 6,069,932 A | 5/2000 | Peshkin et al. | |
| 6,167,145 A | 12/2000 | Foley et al. | |
| 6,198,794 B1 | 3/2001 | Peshkin et al. | |

(Continued)

FOREIGN PATENT DOCUMENTS
EP 0 427 358 A1 5/1991
(Continued)

OTHER PUBLICATIONS

Nobuhiko Sugano, "Computer-assisted orthopedic surgery", 2003, J Orthopaedic Sci, 8: 442-448.*

*Primary Examiner* — Tse Chen
*Assistant Examiner* — Jason Ip
(74) *Attorney, Agent, or Firm* — Taft, Stettinius & Hollister, LLP; Ryan O. White

(57) ABSTRACT

A modeling method for use in surgical navigation is provided. The method acquires a finite number of pre-defined points from a patient's bone and registers the points with a surgical navigation system. The navigation system generates and displays a three-dimensional image of a warped bone model that is manipulatable and accurate in at least the locations of the points taken and can be used to calculate the locations of bone cuts, implant positions and sizes, as well as display all of this information on the three-dimensional warped model.

14 Claims, 17 Drawing Sheets

U.S. PATENT DOCUMENTS

| | | |
|---|---|---|
| 6,205,411 B1 | 3/2001 | DiGioia, III et al. |
| 6,235,038 B1 | 5/2001 | Hunter et al. |
| 6,381,485 B1 | 4/2002 | Hunter et al. |
| 6,402,762 B2 | 6/2002 | Hunter et al. |
| 6,423,077 B2 * | 7/2002 | Carol et al. .............. 606/130 |
| 6,428,547 B1 | 8/2002 | Vilsmeier et al. |
| 6,434,415 B1 | 8/2002 | Foley et al. |
| 6,470,207 B1 | 10/2002 | Simon et al. |
| 6,553,152 B1 | 4/2003 | Miller et al. |
| 6,584,174 B2 | 6/2003 | Schubert et al. |
| 6,674,916 B1 | 1/2004 | Deman et al. |
| 6,711,432 B1 * | 3/2004 | Weiss et al. .............. 600/427 |
| 6,724,922 B1 | 4/2004 | Vilsmeier |
| 6,754,374 B1 | 6/2004 | Miller et al. |
| 6,772,002 B2 | 8/2004 | Schmidt et al. |
| 6,776,526 B2 | 8/2004 | Zeiss |
| 6,782,287 B2 | 8/2004 | Grzeszczuk et al. |
| 6,856,826 B2 | 2/2005 | Seeley et al. |
| 6,856,827 B2 | 2/2005 | Seeley et al. |
| 6,892,088 B2 | 5/2005 | Faulkner et al. |
| 6,895,268 B1 | 5/2005 | Rahn et al. |
| 6,926,673 B2 | 8/2005 | Roberts et al. |
| 6,947,582 B1 | 9/2005 | Vilsmeier et al. |
| 6,978,166 B2 | 12/2005 | Foley et al. |
| 6,990,220 B2 | 1/2006 | Ellis et al. |
| 7,010,095 B2 | 3/2006 | Mitschke et al. |
| 2001/0007918 A1 | 7/2001 | Vilsmeier |
| 2001/0011175 A1 | 8/2001 | Hunter et al. |
| 2002/0183610 A1 | 12/2002 | Foley et al. |
| 2003/0059097 A1 | 3/2003 | Abovitz et al. |
| 2004/0030245 A1 | 2/2004 | Noble et al. |
| 2004/0087852 A1 | 5/2004 | Chen et al. |
| 2004/0127788 A1 | 7/2004 | Arata |
| 2005/0015003 A1 | 1/2005 | Lachner et al. |
| 2005/0015022 A1 | 1/2005 | Richard et al. |
| 2005/0015099 A1 | 1/2005 | Momoi et al. |
| 2005/0020911 A1 | 1/2005 | Viswanathan et al. |
| 2005/0021043 A1 | 1/2005 | Jansen et al. |
| 2005/0021044 A1 | 1/2005 | Stone et al. |
| 2005/0033117 A1 | 2/2005 | Ozaki et al. |
| 2005/0033149 A1 | 2/2005 | Strommer et al. |
| 2005/0038337 A1 | 2/2005 | Edwards |
| 2005/0049477 A1 | 3/2005 | Fu et al. |
| 2005/0049478 A1 | 3/2005 | Kuduvalli et al. |
| 2005/0049486 A1 | 3/2005 | Urquhart et al. |
| 2005/0054915 A1 | 3/2005 | Sukovic et al. |
| 2005/0054916 A1 | 3/2005 | Mostafavi |
| 2005/0059873 A1 | 3/2005 | Glozman et al. |
| 2005/0085714 A1 | 4/2005 | Foley et al. |
| 2005/0085715 A1 | 4/2005 | Dukesherer et al. |
| 2005/0085717 A1 | 4/2005 | Shahidi |
| 2005/0085718 A1 | 4/2005 | Shahidi |
| 2005/0085720 A1 | 4/2005 | Jascob et al. |
| 2005/0090730 A1 | 4/2005 | Cortinovis et al. |
| 2005/0090733 A1 | 4/2005 | Van Der Lugt et al. |
| 2005/0096515 A1 | 5/2005 | Geng |
| 2005/0096535 A1 | 5/2005 | De la Barrera |
| 2005/0101970 A1 | 5/2005 | Rosenberg |
| 2005/0113960 A1 | 5/2005 | Karau et al. |
| 2005/0119561 A1 | 6/2005 | Kienzle, III |
| 2005/0119565 A1 | 6/2005 | Pescatore |
| 2005/0119639 A1 | 6/2005 | McCombs et al. |
| 2005/0124988 A1 | 6/2005 | Terrill-Grisoni et al. |
| 2005/0137599 A1 | 6/2005 | Masini |
| 2005/0148850 A1 | 7/2005 | Lahm et al. |
| 2005/0148855 A1 | 7/2005 | Kienzle, III |
| 2005/0197568 A1 | 9/2005 | Vass et al. |
| 2005/0197569 A1 | 9/2005 | McCombs |
| 2005/0203373 A1 | 9/2005 | Boese et al. |
| 2005/0203374 A1 | 9/2005 | Vilsmeier |
| 2005/0203375 A1 | 9/2005 | Willis et al. |
| 2005/0203383 A1 | 9/2005 | Moctezuma de la Barrera et al. |
| 2005/0203384 A1 | 9/2005 | Sati et al. |
| 2005/0215879 A1 | 9/2005 | Chuanggui |
| 2005/0216032 A1 | 9/2005 | Hayden |
| 2005/0228250 A1 | 10/2005 | Bitter et al. |
| 2005/0228270 A1 | 10/2005 | Lloyd et al. |
| 2005/0228404 A1 | 10/2005 | Vandevelde |
| 2005/0234335 A1 | 10/2005 | Simon et al. |
| 2005/0251026 A1 | 11/2005 | Stone |
| 2005/0251030 A1 | 11/2005 | Azar et al. |
| 2005/0277832 A1 | 12/2005 | Foley et al. |
| 2005/0288575 A1 | 12/2005 | de la Barrera et al. |
| 2005/0288578 A1 | 12/2005 | Durlak |
| 2006/0004284 A1 | 1/2006 | Grunschlager et al. |
| 2006/0009780 A1 | 1/2006 | Foley et al. |
| 2006/0015030 A1 | 1/2006 | Poulin et al. |
| 2006/0025677 A1 | 2/2006 | Verard et al. |
| 2006/0036149 A1 | 2/2006 | Lavigna et al. |
| 2006/0036151 A1 | 2/2006 | Ferre et al. |
| 2006/0036162 A1 | 2/2006 | Shahidi et al. |
| 2006/0058604 A1 | 3/2006 | Avinash et al. |
| 2006/0058615 A1 | 3/2006 | Mahajan et al. |
| 2006/0058616 A1 | 3/2006 | Marquart et al. |
| 2006/0058644 A1 | 3/2006 | Hoppe et al. |

FOREIGN PATENT DOCUMENTS

| | | |
|---|---|---|
| EP | 0 649 117 A2 | 4/1995 |
| EP | 1 226 788 A1 | 7/2002 |
| GB | 2 246 936 A | 2/1992 |
| WO | WO 02/062248 A1 | 8/2002 |
| WO | WO 04/001569 A2 | 12/2003 |
| WO | WO 2004/006770 A2 | 1/2004 |
| WO | WO 2004/069036 A2 | 8/2004 |

* cited by examiner

MODELING METHOD AND APPARATUS FOR USE IN SURGICAL NAVIGATION

RELATED APPLICATIONS

This application claims priority to U.S. Provisional Patent Application Ser. No. 60/784,879, filed Mar. 22, 2006, the disclosure of which is expressly incorporated herein in its entirety by this reference.

FIELD OF THE INVENTION

The present teachings relate generally to surgical navigation and more particularly to a method of creating a three-dimensional bone model that is based upon specific reproducible landmarks on the patient's anatomy.

BACKGROUND

Surgical navigation systems, also known as computer assisted surgery and image guided surgery, aid surgeons in locating patient anatomical structures, guiding surgical instruments, and implanting medical devices with a high degree of accuracy. Surgical navigation has been compared to a global positioning system that aids vehicle operators to navigate the earth. A surgical navigation system typically includes a computer, a tracking system, and patient anatomical information. The patient anatomical information can be obtained by using an imaging mode such as fluoroscopy, computer tomography (CT) or simply by defining locations on the patient's anatomy with the surgical navigation system. Surgical navigation systems can be used for a wide variety of surgeries to improve patient outcomes.

To successfully implant a medical device, surgical navigation systems often employ various forms of computing technology, as well as utilize intelligent instruments, digital touch devices, and advanced 3-D visualization software programs. All of these components enable surgeons to perform a wide variety of standard and minimally invasive surgical procedures and techniques. Moreover, these systems allow surgeons to more accurately plan, track and navigate the placement of instruments and implants relative to a patient's body, as well as conduct pre-operative and intra-operative body imaging.

To accomplish the accurate planning, tracking and navigation of surgical instruments, tools and/or medical devices during a surgical navigation procedure, surgeons often utilize "tracking arrays" that are coupled to the surgical components. The tracking arrays allow the surgeon to accurately track the location of these surgical components, as well as the patient's bones during the surgery. By knowing the physical location of the tracking array, the software detection program of the tracking system is able to calculate the position of the tracked component relative to a surgical plan image.

It is known to employ bone morphing techniques in which points on the surface of a bone, for instance, a femur, are collected to create a three-dimensional patient bone surface. That is, a virtual representation of the bone is created by acquiring the spatial position coordinates corresponding to several points collected on the surface of the bone, and subsequently mapping the spatial position coordinates to create a digital model of the bone. This technique is sometimes referred to as "painting." This painted surface is then compared to a series of bone models and the model most closely resembling the surface is chosen. The chosen bone model is then scaled three-dimensionally such that the database model matches the patient's anatomy in those regions that were painted. The "morphed" database model is then displayed to the surgeon on a monitor. While this technique is generally useful for generating a representative bone model of a patient undergoing a surgical navigation process, the process has limitations. For instance, many surgeons find these morphing processes to be too expensive, cumbersome and time-consuming for wide acceptance and regular use. Thus, it would be desirable to overcome these and other shortcomings of the prior art.

SUMMARY OF THE INVENTION

The present invention provides an efficient modeling method and apparatus for use in surgical navigation. Embodiments incorporating the present invention require only a finite number of pre-defined points to be taken from a patient's bone and registered with a surgical navigation system. The inventive navigation system then generates and displays a three-dimensional ("3-D") image of a warped bone model that is manipulatable and accurate in at least the locations of the points taken. The system can calculate the locations of bone cuts, implant positions and sizes, and display all of this on the 3-D warped model.

In one form thereof, the present invention provides a method of modeling a bone during a surgical navigation procedure. A surgical navigation system having a tracking system, a computer having a bone model stored therein, a monitor, and a tool to acquire points on a bone are all provided. In this inventive method, a finite number of pre-defined points are acquired from a bone with a tool such as a tracked probe. The reference frame defined by the acquired points is aligned with the reference frame of the bone model that is stored in the system. Using an algorithm, the system then warps or deforms the bone model to coincide with the location of the pre-defined points. The monitor displays a three-dimensional and manipulatable warped model. The display also includes images of the predefined points. In this method, the displayed warped model accurately represents the location of the patient's bone in real time at the locations of the predefined points.

In exemplary embodiments, less than about ten pre-defined points or even less than about seven points are acquired. Generally, only as many landmarks or pre-defined points as are needed to completely categorize the bone for calculation of bone cuts, implant sizing and placement, etc. are acquired. Since only a select number of points are required, the time needed to acquire the points and complete the procedure is reduced, in contrast to known painting techniques described above. Reducing the time taken for the procedure also, of course, reduces the time the patient is exposed to infection risks. Furthermore, even though the 3-D displayed warped model is only known to be accurate in the locations of the pre-defined points, which are also displayed, the model nonetheless provides a helpful visualization tool for the surgeon. Accuracy is only needed in those specific areas that are actually used by the system to calculate bone cuts and implant sizing.

According to one exemplary embodiment herein, a method of modeling a bone during a surgical navigation procedure is provided. The method comprises providing a tracking system and a modeling instrument detectable by the tracking system; acquiring a finite number of predefined points from a bone with the modeling instrument, the acquired points being used to generate a representative model of the bone; associating the representative model of the bone with a reference bone model from a computer database associated with the tracking system; warping the reference bone model to at least coincide with the representative model of the bone at the locations of the acquired predefined points; and displaying a three-dimensional and manipulatable image of the warped reference bone model, the image showing the acquired predefined points. According to this embodiment, the displayed warped reference bone model accurately represents the location of the patient's bone in real time in at least the locations of the acquired predefined points.

According to another exemplary embodiment herein, an image guided surgery system is provided. The system comprises a tracking system having a measurement field; a modeling instrument detectable by the tracking system when exposed to the measurement field; a means for generating a representative model of a bone while the modeling instrument acquires a finite number of predefined points from the bone; a means for associating the representative model of the bone with a reference bone model contained within a computer database that is associated with the tracking system; a means for warping the reference bone model to at least coincide with the representative bone model at the locations of the acquired predefined points; and a means for displaying a three-dimensional and manipulatable image of the warped reference bone model, the image accurately showing the location of the patient's bone in real time in at least the locations of the acquired predefined points.

In yet another exemplary embodiment in accordance with the present invention, a computer readable storage medium modeling process is provided. According to this embodiment, the computer readable storage medium stores instructions that, when executed by a computer, causes the computer to perform the modeling process on a bone during a surgical navigation procedure. The modeling process comprises the following steps: detecting a modeling instrument with a tracking system when the modeling instrument is exposed to a measurement field of the tracking system; generating a representative model of a bone while the modeling instrument acquires a finite number of predefined points from the bone; associating the representative model of the bone with a reference bone model contained on a computer database associated with the tracking system; warping the reference bone model to at least coincide with the representative bone model at the locations of the acquired predefined points; and displaying a three-dimensional and manipulatable image of the warped reference bone model, wherein the image accurately shows the location of the patient's bone in real time in at least the locations of the acquired predefined points.

BRIEF DESCRIPTION OF DRAWINGS

The above-mentioned aspects of the present teachings and the manner of obtaining them will become more apparent and the teachings will be better understood by reference to the following description of the embodiments taken in conjunction with the accompanying drawings, wherein.

Corresponding reference characters indicate corresponding parts throughout the several views.

DETAILED DESCRIPTION

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

Figure 1:
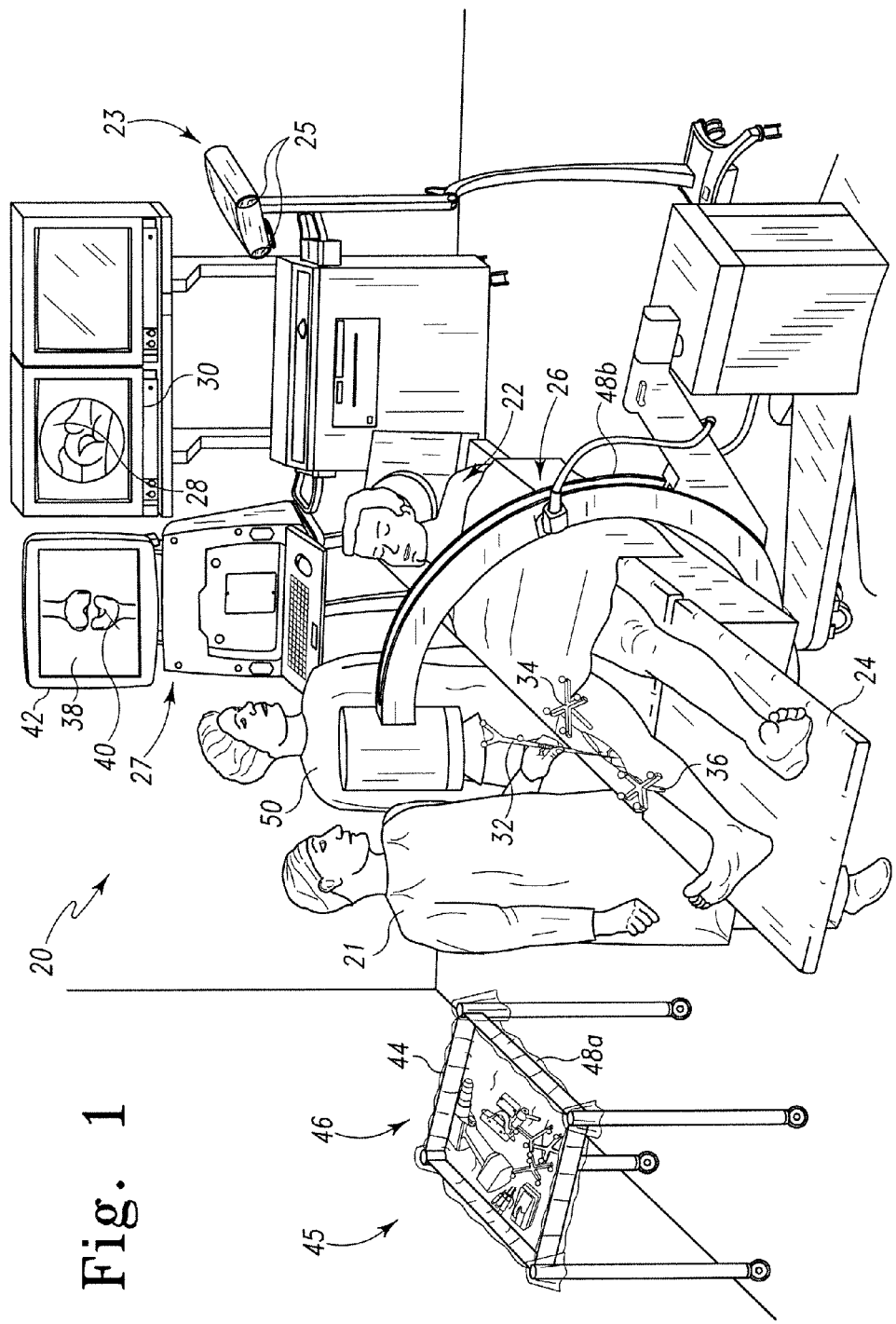
FIG. 1 is a perspective view of an operating room setup in a surgical navigation embodiment in accordance with the present teachings.

FIG. 1 shows a perspective view of an operating room with surgical navigation system 20. Surgeon 21 is aided by the surgical navigation system in performing knee arthroplasty, also known as knee replacement surgery, on patient 22 shown lying on operating table 24. Surgical navigation system 20 has a tracking system that locates arrays and tracks them in real-time. To accomplish this, the surgical navigation system includes optical locator 23, which has two CCD (charge couple device) cameras 25 that detect the positions of the arrays in space by using triangulation methods. The relative location of the tracked arrays, including the patient's anatomy, can then be shown on a computer display (such as computer display 27 for instance) to assist the surgeon during the surgical procedure. The arrays that are typically used include probe arrays, instrument arrays, reference arrays, and calibrator arrays. The operating room includes an imaging system such as C-arm fluoroscope 26 with fluoroscope display image 28 to show a real-time image of the patient's knee on monitor 30. Surgeon 21 uses surgical probe 32 to reference a point on the patient's knee, and reference arrays 34, 36 attached to the patient's femur and tibia to provide known anatomic reference points so the surgical navigation system can compensate for leg movement. The relative location of probe array 32 to the patient's tibia is then shown as reference numeral 40 on computer display image 38 of computer monitor 42. The operating room also includes instrument cart 45 having tray 44 for holding a variety of surgical instruments and arrays 46. Instrument cart 45 and C-arm 26 are typically draped in sterile covers 48a, 48b to eliminate contamination risks within the sterile field.

The surgery is performed within a sterile field, adhering to the principles of asepsis by all scrubbed persons in the operating room. Patient 22, surgeon 21 and assisting clinician 50 are prepared for the sterile field through appropriate scrubbing and clothing. The sterile field will typically extend from operating table 24 upward in the operating room. Typically both computer display image 38 and fluoroscope display image 28 are located outside of the sterile field.

A representation of the patient's anatomy can be acquired with an imaging system, a virtual image, a morphed image, or a combination of imaging techniques. The imaging system can be any system capable of producing images that represent the patient's anatomy such as a fluoroscope producing x-ray two-dimensional images, computer tomography (CT) producing a three-dimensional image, magnetic resonance imaging (MRI) producing a three-dimensional image, ultrasound imaging producing a two-dimensional image, and the like. A virtual image of the patient's anatomy can be created by defining anatomical points with surgical navigation system 20 or by applying a statistical anatomical model. A morphed image of the patient's anatomy can be created by combining an image of the patient's anatomy with a data set, such as a virtual image of the patient's anatomy. Some imaging systems, such as C-arm fluoroscope 26, can require calibration. The C-arm can be calibrated with a calibration grid that enables determination of fluoroscope projection parameters for different orientations of the C-arm to reduce distortion. A registration phantom can also be used with a C-arm to coordinate images with the surgical navigation application program and improve scaling through the registration of the C-arm with the surgical navigation system. A more detailed description of a C-arm based navigation system is provided in James B. Stiehl et al., Navigation and Robotics in Total Joint and Spine Surgery, Chapter 3 C-Arm-Based Navigation, Springer-Verlag (2004).

Figure 2:
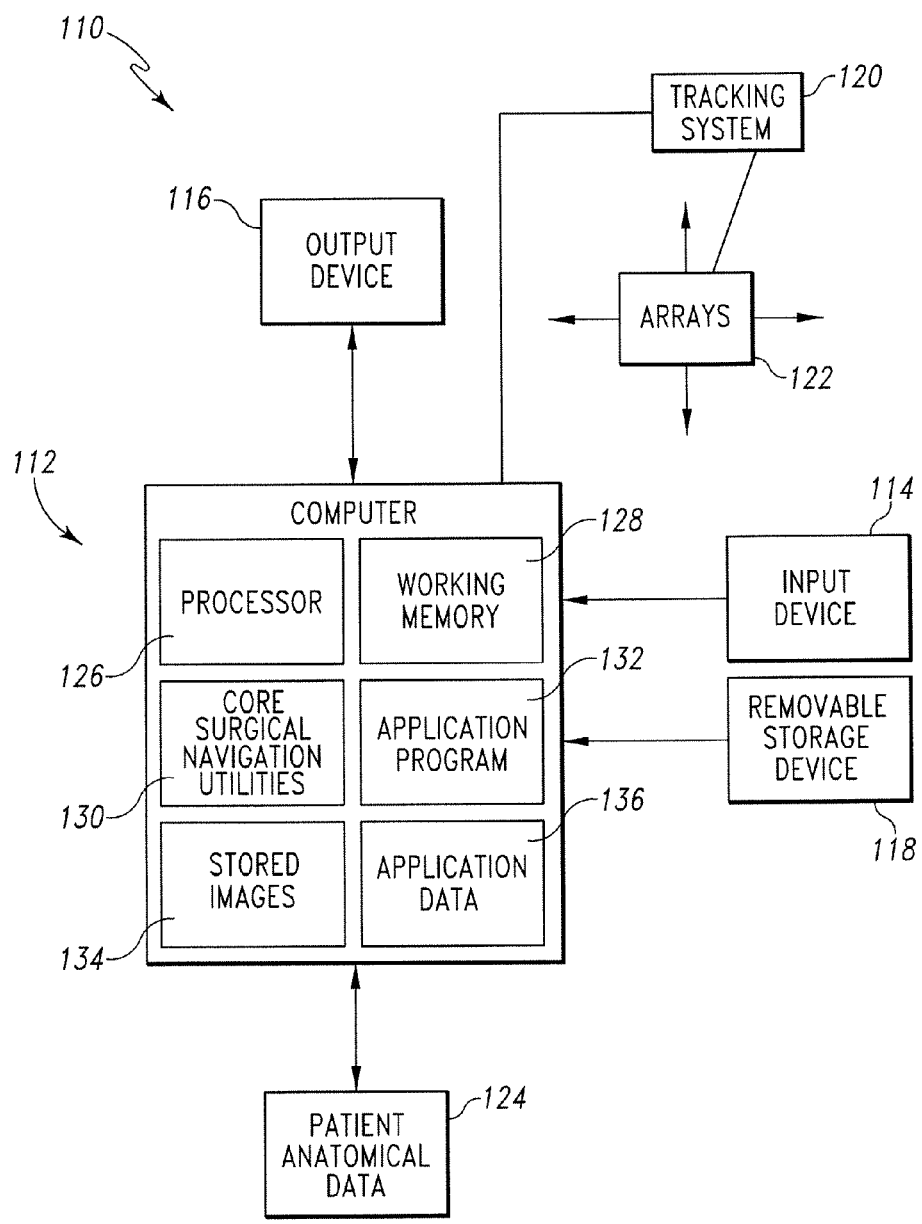
FIG. 2 is an exemplary block diagram of a surgical navigation system embodiment in accordance with the present teachings.

FIG. 2 is a block diagram of an exemplary surgical navigation system embodiment in accordance with the present teachings, such as an Acumen™ Surgical Navigation System, available from EBI, L.P., Parsippany, N.J. USA, a Biomet Company. The surgical navigation system 110 comprises computer 112, input device 114, output device 116, removable storage device 118, tracking system 120, arrays 122, and patient anatomical data 124, as further described in the brochure Acumen™ Surgical Navigation System, Understanding Surgical Navigation (2003) available from EBI, L.P. The Acumen™ Surgical Navigation System can operate in a variety of imaging modes such as a fluoroscopy mode creating a two-dimensional x-ray image, a computer-tomography (CT) mode creating a three-dimensional image, and an imageless mode creating a virtual image or planes and axes by defining anatomical points of the patient's anatomy. In the imageless mode, a separate imaging device such as a C-arm is not required, thereby simplifying set-up. The Acumen™ Surgical Navigation System can run a variety of orthopedic applications, including applications for knee arthroplasty, hip arthroplasty, spine surgery, and trauma surgery, as further described in the brochure "Acumen™ Surgical Navigation System, Surgical Navigation Applications" (2003), available from EBI, L.P. A more detailed description of an exemplary surgical navigation system is provided in James B. Stiehl et al., Navigation and Robotics in Total Joint and Spine Surgery, Chapter 1: Basics of Computer-Assisted Orthopedic Surgery (CAOS), Springer-Verlag (2004).

Computer 112 can be any computer capable of properly operating surgical navigation devices and software, such as a computer similar to a commercially available personal computer that comprises a processor 126, working memory 128, core surgical navigation utilities 130, an application program 132, stored images 134, and application data 136. Processor 126 is a processor of sufficient power for computer 112 to perform desired functions, such as one or more microprocessors. Working memory 128 is memory sufficient for computer 112 to perform desired functions such as solid-state memory, random-access memory, and the like. Core surgical navigation utilities 130 are the basic operating programs, and include image registration, image acquisition, location algorithms, orientation algorithms, virtual keypad, diagnostics, and the like. Application program 132 can be any program configured for a specific surgical navigation purpose, such as orthopedic application programs for unicondylar knee ("uni-knee"), total knee, hip, spine, trauma, intramedullary ("IM") nail/rod, and external fixator. Stored images 134 are those recorded during image acquisition using any of the imaging systems previously discussed. Application data 136 is data that is generated or used by application program 132, such as implant geometries, instrument geometries, surgical defaults, patient landmarks, and the like. Application data 136 can be pre-loaded in the software or input by the user during a surgical navigation procedure.

Output device 116 can be any device capable of creating an output useful for surgery, such as a visual output and an auditory output. The visual output device can be any device capable of creating a visual output useful for surgery, such as a two-dimensional image, a three-dimensional image, a holographic image, and the like. The visual output device can be a monitor for producing two and three-dimensional images, a projector for producing two and three-dimensional images, and indicator lights. The auditory output can be any device capable of creating an auditory output used for surgery, such as a speaker that can be used to provide a voice or tone output.

Removable storage device 118 can be any device having a removable storage media that would allow downloading data, such as application data 136 and patient anatomical data 124. The removable storage device can be a read-write compact disc (CD) drive, a read-write digital video disc (DVD) drive, a flash solid-state memory port, a removable hard drive, a floppy disc drive, and the like.

Tracking system 120 can be any system that can determine the three-dimensional location of devices carrying or incorporating markers that serve as tracking indicia. An active tracking system has a collection of infrared light emitting diode (ILEDs) illuminators that surround the position sensor lenses to flood a measurement field of view with infrared light. A passive system incorporates retro-reflective markers that reflect infrared light back to the position sensor, and the system triangulates the real-time position (x, y, and z location) and orientation (rotation around x, y, and z axes) of an array 122 and reports the result to the computer system with an accuracy of about 0.35 mm Root Mean Squared (RMS). An example of a passive tracking system is a Polaris® Passive System and an example of a marker is the NDI Passive Spheres™, both available from Northern Digital Inc. Ontario, Canada. A hybrid tracking system can detect active and active wireless markers in addition to passive markers. Active marker based instruments enable automatic tool identification, program control of visible LEDs, and input via tool buttons. An example of a hybrid tracking system is the Polaris® Hybrid System, available from Northern Digital Inc. A marker can be a passive IR reflector, an active IR emitter, an electromagnetic marker, and an optical marker used with an optical camera.

As is generally known within the art, implants and instruments may also be tracked by electromagnetic tracking systems. These systems locate and track devices and produce a real-time, three-dimensional video display of the surgical procedure. This is accomplished by using electromagnetic field transmitters that generate a local magnetic field around the patient's anatomy. In turn, the localization system includes magnetic sensors that identify the position of tracked instruments as they move relative to the patient's anatomy. By not requiring a line of sight with the transmitter, electromagnetic systems are also adapted for in vivo use, and are also integrable, for instance, with ultrasound and CT imaging processes for performing interventional procedures by incorporating miniaturized tracking sensors into surgical instruments. By processing transmitted signals generated by the tracking sensors, the system is able to determine the position of the surgical instruments in space, as well as superimpose their relative positions onto pre-operatively captured CT images of the patient.

Arrays 122 can be probe arrays, instrument arrays, reference arrays, calibrator arrays, and the like. Arrays 122 can have any number of markers, but typically have three or more markers to define real-time position (x, y, and z location) and orientation (rotation around x, y, and z axes). An array comprises a body and markers. The body comprises an area for spatial separation of the markers. In some embodiments, there are at least two arms and some embodiments can have three arms, four arms, or more. The arms are typically arranged asymmetrically to facilitate specific array and marker identification by the tracking system. In other embodiments, such as a calibrator array, the body provides sufficient area for spatial separation of markers without the need for arms. Arrays can be disposable or non-disposable. Disposable arrays are typically manufactured from plastic and include installed markers. Non-disposable arrays are manufactured from a material that can be sterilized, such as aluminum, stainless steel, and the like. The markers are removable, so they can be removed before sterilization.

Planning and collecting patient anatomical data 124 is a process by which a clinician inputs into the surgical navigation system actual or approximate anatomical data. Anatomical data can be obtained through techniques such as anatomic painting, bone morphing, CT data input, and other inputs, such as ultrasound and fluoroscope and other imaging systems.

Figure 3:
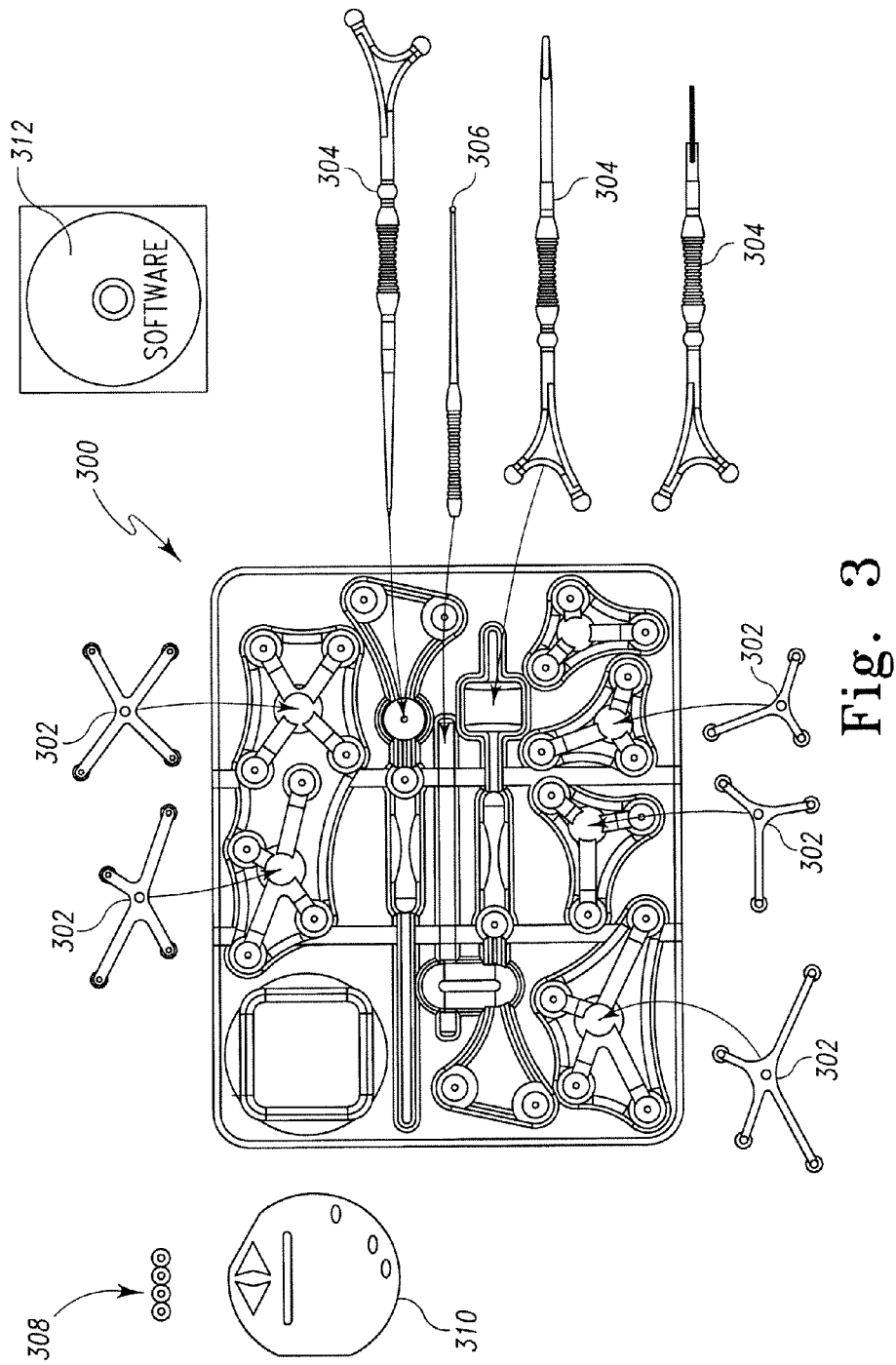
FIG. 3 is an exemplary surgical navigation kit embodiment in accordance with the present teachings.

FIG. 3 shows orthopedic application kit 300, which is used in accordance with the present teachings. Application kit 300 is typically carried in a sterile bubble pack and is configured for a specific surgery. Exemplary kit 300 comprises arrays 302, surgical probes 304, stylus 306, markers 308, virtual keypad template 310, and application program 312. Orthopedic application kits are available for unicondylar knee, total knee, total hip, spine, and external fixation from EBI, L.P.

The present teachings enhance the above-described surgical navigation process by incorporating a bone landmark registration and warping process into surgical navigation system 20. More particularly, in addition to tracking surgical components, the navigation system can also generate a three-dimensional model of a patient's bone by intra-operatively acquiring individual surface landmarks on the patient's anatomy with a surgical probe or similar instrument that is detected and tracked by the navigation system. By acquiring these landmarks and registering them with the navigation system's computer, a surgeon can accurately navigate a biomedical implant to an intra-operatively planned position, as well as gather important surgical information, such as gap analysis data, resection plane details and bone alignment angles.

As is appreciated by those within the art, bony landmarks are visible points or locations on a patient's anatomy which are identifiable by referencing known locations on the surface of the bone. For instance, known bony landmarks on the femur include, but are not limited to, the medial/lateral condyles, medial/lateral epicondyles, medial/lateral posterior condyles, and the anterior cortex. Similar bony landmarks are also found on other bones (such as the tibia, fibula, patella and pelvis, for instance), however, for simplicity purposes, the exemplary illustrations provided here are specifically directed to the femur. As the present teachings are not intended to be limiting, it should be understood and appreciated that these teachings are also applicable to bony structures other than the femur.

Generally speaking, the present teachings are directed to methods for generating three-dimensional bone models having a 1:1 ratio between specific reproducible landmarks from a bone to the equivalent on a representative bone model stored in navigation system's computer database. Each database bone model has only as many landmarks as is needed to completely categorize the bone as it is used in a given surgical operation. For example, in some exemplary embodiments less than about ten pre-defined points are acquired to categorize the bone. In other exemplary embodiments, less than about seven points are acquired to categorize the bone. When all the necessary points (coordinates) are gathered from the patient's bone, these coordinates create a reference frame of acquired points that then replaces a reference frame of points on the representative database bone model. The database model is then warped or scaled using special rules or algorithms to match the patient's critical landmark areas that have been acquired by the navigation system.

Figure 4:
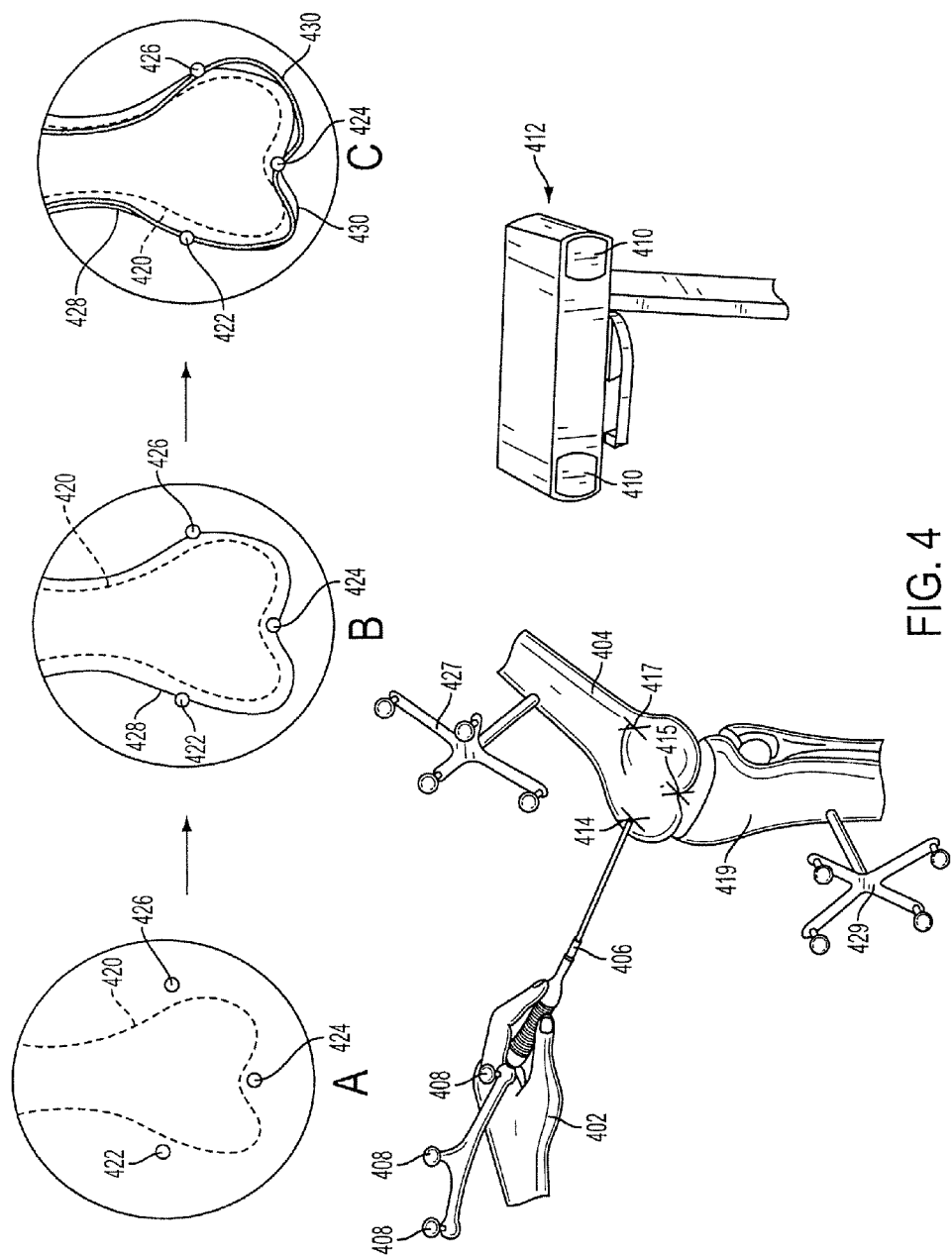
FIG. 4 is a fragmentary perspective view illustrating an exemplary femoral landmark registration warping process in accordance with the present teachings.

The principles upon which exemplary embodiments of the present invention rely can be understood with reference to FIG. 4, which illustrates three images, A, B and C. It should be understood that these images are merely intended to illustrate general principles, and are not representative of any particular screen shot that a surgeon may view during a surgical navigation procedure. For a total knee arthroplasty (TKA), for example, the database of the surgical navigation system includes one or more "generic" models of a femur. To illustrate these general principles, an embodiment with only one model will suffice.

Turning to image A, generic model 420, that is stored in the navigation system, is fairly representative of an average femur. Indeed, aside from relative size and proportion, the differences in the human skeleton from patient to patient are relatively small. In exemplary embodiments, the surgical navigation system will prompt the operating surgeon to acquire several points, one-by-one, at select locations (known anatomical landmarks) on the tracked femur, using a tracked probe or other suitable instrument. To select or acquire these landmarks, a navigational application program is typically used which arranges the point acquisition process into sequential pages of surgical protocol that are configured according to a graphic user interface scheme. These points could include, among others, the distal femur, lateral and medial condyles, to name only a few. For instance, here, surgeon 402 has touched surgical probe 406 against the surface of femur 404 at three landmark locations 414, 415 and 417. As the surgeon positions the surgical probe at these various landmarks, the tracking system tracks the probe's markers 408 with cameras 410 of optical locator 412 and detects the position of the markers in space. To detect the location of surgical probe 406 relative to femur 404 and tibia 419, the tracking system references the position of markers 408 as they move with respect to reference arrays 427 and 429, which are fixably attached to the femur and tibia of the patient. By tracking the position of the markers relative to femur 404, the exact location of the landmarks can be determined and shown on the surgical plan image (shown here as points 422, 424 and 426). Once the probe is positioned at a point to be acquired, the point can be selected by blocking the probe from the camera or by other input means to the system.

Turning to image B, the surgical navigation system is programmed to deform or "warp" femur model 420 such that it fits at least the points (422, 424 and 426) that have been acquired. For example, in image B, warped model 428 fits all three points 422, 424 and 426. In the simplest embodiment, the algorithm that warps model 420 into model 428 performs a uniform scaling, not unlike a photocopier that reduces or enlarges a 2-dimensional image. In other embodiments, more sophisticated transformations are performed on the generic model, which may include skewing, non-linear scaling, squeezing, affine transformations and the like. One of skill in the art would readily recognize many different approaches that can be used to deform the model to match the acquired points. Additional information further illustrating exemplary rules and algorithms that may be employed to warp generic bone models in accordance with certain embodiments of the present teachings is provided within the Examples section below. Moreover, a more detailed description of an exemplary surgical morphing process can be found in James B. Stiehl et al., Navigation and Robotics in Total Joint and Spine Surgery, Chapter 5: Bone Morphing: 3D Reconstruction Without Pre- or Intraoperative Imaging—Concept and Applications, Springer-Verlag (2004). Both of the above-referenced disclosures are expressly incorporated by reference herein.

One of skill in the art should understand that many algorithms are possible that will meet the basic objectives of displaying a femur model in three-dimensions that is accurate in at least the positions of the points taken and that such displayed model at least has the general appearance of a femur. The latter objective is thought to be most helpful to the surgeon, even though the surgeon is instructed by this inventive system that the displayed three-dimensional model is only known to be accurate at the positions of the points that were earlier acquired and that are displayed on the warped model.

Indeed, image C illustrates the location of the patient's actual femur 430. As illustrated, the location of actual femur 430 and warped femur model 428 coincide at points 422, 424 and 426. The positions also happen to coincide at other locations as well. Nonetheless, the warped model is only known to be accurate in the locations where actual points are taken. As shown in illustration C, even though warped model 428 is inaccurate at locations other than the three points just noted, it still provides a useful visual aid for the physician. Further, as described in more detail below, the surgical navigation system generates three-dimensional image models that can be manipulated by the surgeon intra-operatively, and which also display the accurate position of the points that have been taken and entered into the system.

The idea behind embodiments of the present invention incorporating the principles just noted is that surgical navigation systems (even known systems whose displayed models are accurate in areas beyond a small number of points) only use a finite number of points to calculate all cuts that are made to the bone, as well as implant sizing and positioning. That is, accuracy beyond these finite points may be displayed to the surgeon, but are not used in the algorithm that determines the bone cut positions and/or the implant sizing or rotational details.

Embodiments disclosed herein offer a fast and accurate means of registering a patient undergoing computer assisted surgery in which a representative bone model is required for visualization, but without requiring preoperative imaging, intraoperative imaging, or surface painting/surface matching algorithms. As can be appreciated by those in the art, a navigation system is only as accurate as the patient information it receives. Processes which require the surgeon to acquire numerous points to create an accurate surface model are not only time-consuming, but can also lead the surgeon to believe that other areas of the model are accurate when in fact they are not. The present teachings offer visualization and ease-of-use without compromising accuracy and without requiring the registration of numerous points.

To better understand and appreciate the present teachings, an exemplary illustration of a femoral landmark registration warping process is now provided. As is known in the art, before implanting a knee prosthetic, the mechanical axis of the femur must first be determined, particularly as the resection performed prior to installing the femoral prosthetic must be aligned in accordance with the orientation of the femur's mechanical axis. The exact position of the resection surfaces of the femur are crucial if the knee prosthetic is to have a long working life. As such, the surgeon must establish the standard bearing surface of the resection plane on the femur according to the geometrical specifications of the knee prosthesis while taking into account the mechanical axis of the femur. In some cases, pathological displacements must also be corrected and allowances must be made for the position and action of the ligaments and muscles that are present.

Figure 5:
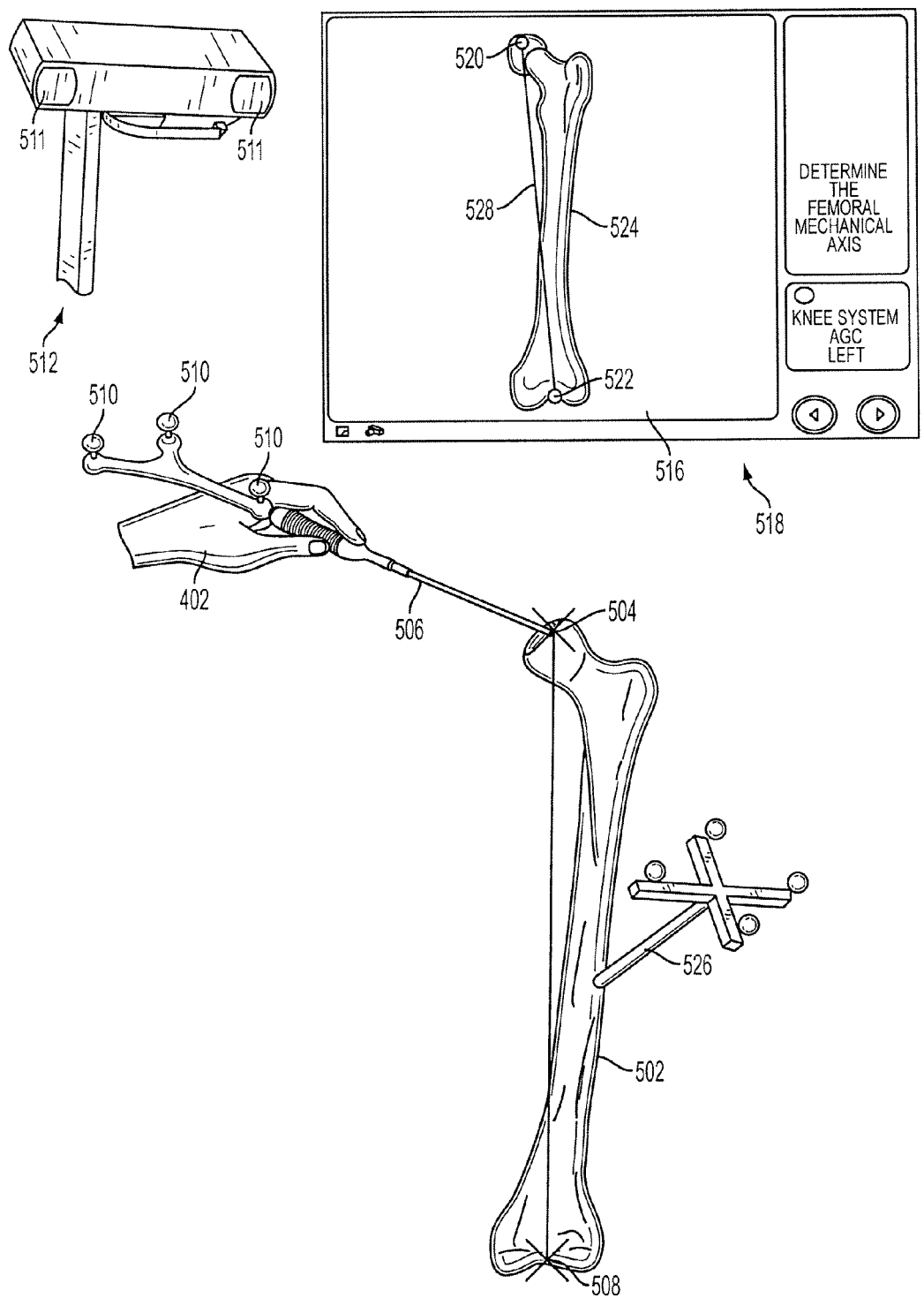
FIG. 5 is a fragmentary perspective view illustrating an exemplary method for determining the mechanical axis of a femur in accordance with the present teachings.

As shown in FIG. 5, surgeon 402 determines the femoral mechanical axis of femur 502 by touching/acquiring surgical probe 506 against the surface of the femur at two individual locations that together form a line defining the femoral mechanical axis, namely a line running from the center of the femoral head 504 (hip center) to the center of the knee 508. Surgical probe 506 includes markers 510, which are identified and tracked by cameras 511 of optical locator 512. As surgeon 402 positions surgical probe 506 at the center of the femoral head 504, as well as the center of the knee 508, the tracking system locates and tracks markers 510 in real-time and detects their position in space by using triangulation methods. The relative locations of the femoral head 504 and knee center 508 are then shown on surgical plan image 516 on computer display 518 as points 520, 522 on representative femur 524. To accomplish this, the tracking system detects the location of surgical probe 506 as it is positioned relative to femur 502 by referencing the position of markers 510 as they move with respect to reference array 526, which is fixably attached to the femur. After the center of the femoral head and the knee are acquired by the surgical probe, a representation of the femoral mechanical axis 528 is then shown on surgical plan image 516 for use by the surgeon.

Figure 6A:
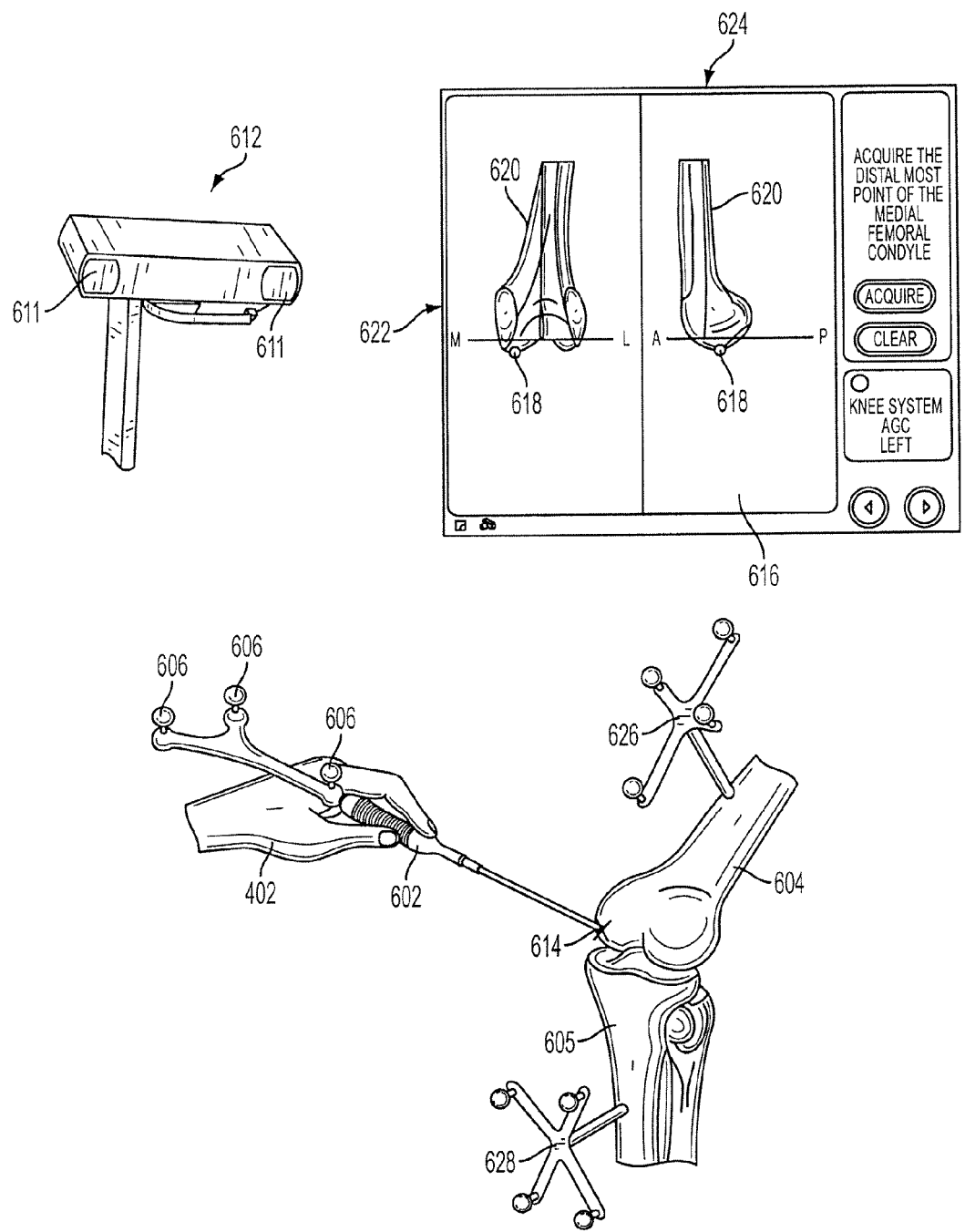
FIG. 6a is a fragmentary perspective view illustrating an exemplary landmark registration for acquiring the distal most point of the medial femoral condyle in accordance with the present teachings.

After the femoral mechanical axis is determined, the surgeon begins acquiring various femoral landmarks. For instance, in FIG. 6a, surgeon 402 acquires the distal most point of the medial femoral condyle. To accomplish this, the navigation system prompts surgeon 402 to place the tip of surgical probe 602 at the location believed to be the most distal point on the medial condyle of femur 604. Thereafter, surgeon 402, based upon experience, identifies a location on the bone representative or characteristic of the desired landmark and places the tip of the probe at this point (represented by reference numeral 614). By knowing the location of markers 606 attached to surgical probe 602, the tracking system, which is defined by cameras 611 of optical locator 612, detects and calculates the position of probe 602 in space relative to femur 604 and projects the medial femoral condyle landmark 614 on surgical plan image 616 as point 618 on representative femur 620, which is shown both from a front view 622 and a side view 624. To generate point 618, the tracking system detects the location of surgical probe 602 as it is positioned relative to femur 604 by referencing the position of markers 606 as they move with respect to reference arrays 626, 628, which are fixably attached to femur 604 and tibia 605.

Figure 6B:
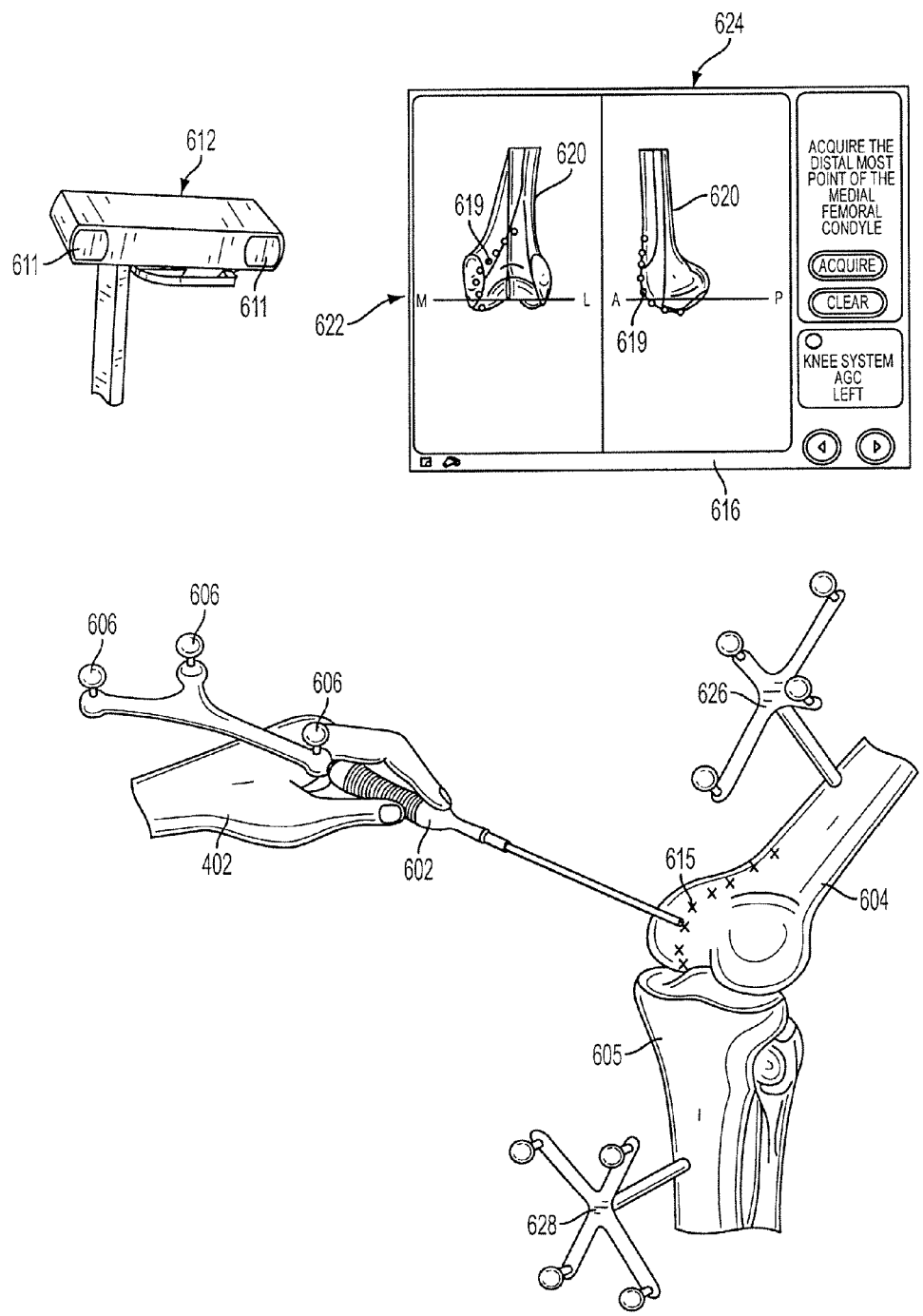
FIG. 6b is a fragmentary perspective view illustrating another exemplary landmark registration for acquiring the distal most point of the medial femoral condyle in accordance with the present teachings.

While the above-referenced process illustrates the surgeon selecting the location of the landmark on the femur, it should also be appreciated that the position of the landmark may also be determined by the navigation system's software. More particularly, and with reference to FIG. 6B, surgeon 402 drags the tip of surgical probe 602 in a linear trajectory 615 (see the line formed by a series of "X's") across the surface of femur 604 in the general region believed to be near the most distal point on the medial femoral condyle. As surgical probe 602 is moved along linear trajectory 615, markers 606 are detected by the tracking system and the spatial position of the probe is calculated relative to the femur and projected on surgical plan image 616 as line 619. Once all of the points defining linear trajectory 615 are collected and registered by the navigation system, the distal most point on the medial femoral condyle is calculated with the computer's software and then displayed on the plan image for the surgeon.

Figure 7:
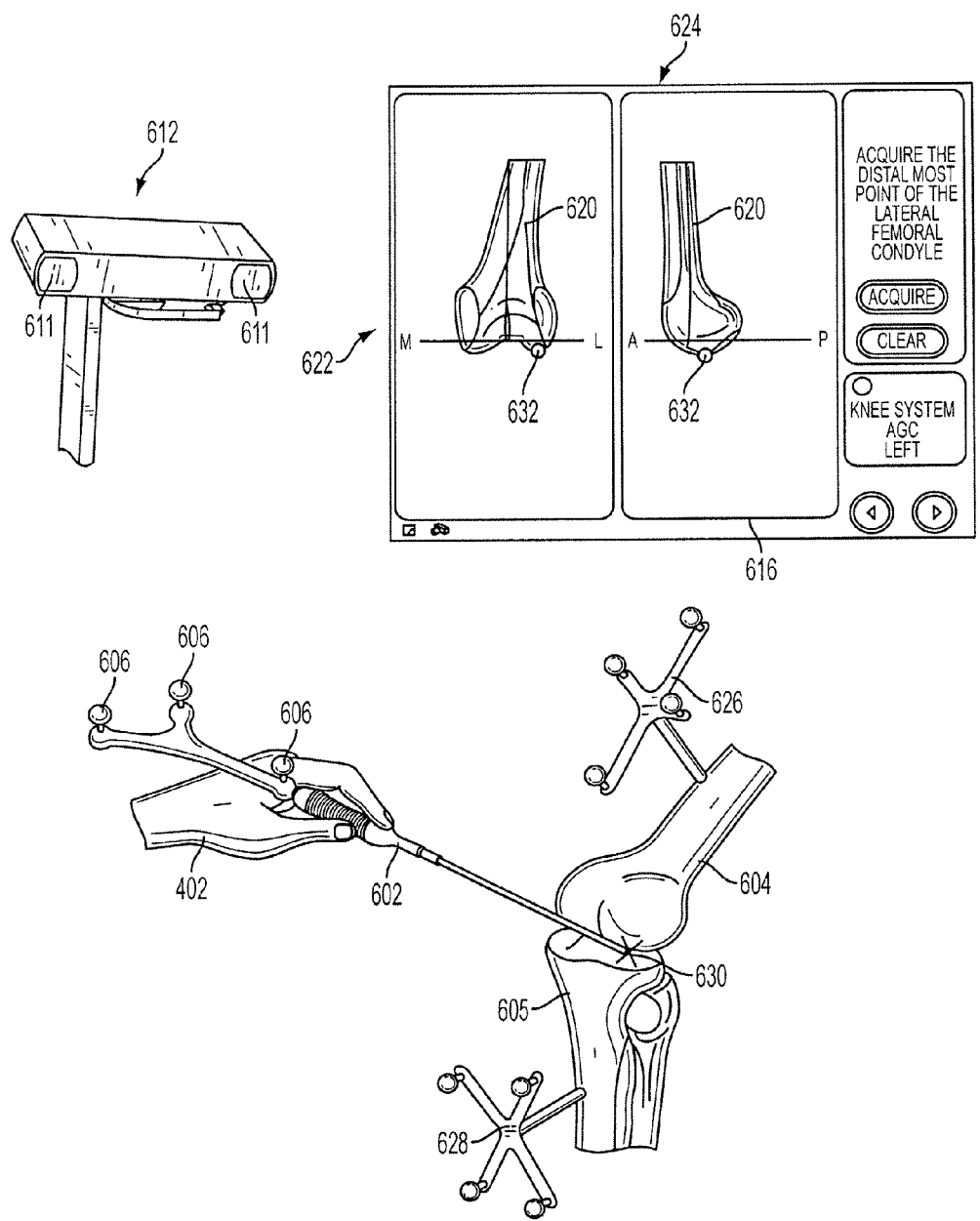
FIG. 7 is a fragmentary perspective view illustrating an exemplary landmark registration for acquiring the distal most point of the lateral femoral condyle in accordance with the present teachings.

After the medial femoral condyle is acquired, the surgeon acquires the lateral femoral condyle, as shown in FIG. 7. To acquire the distal most point of the lateral femoral condyle, the navigation system once again prompts surgeon 402 to place the tip of surgical probe 602 at the location believed to be the most distal point on the lateral condyle of femur 604 (shown here as 630). As explained in detail above, the location of the lateral femoral condyle can either be selected by the surgeon or by the navigation system. However this location is determined, the tracking system must detect and calculate the spatial position of probe 602 as it is positioned relative to femur 604 before projecting the point (632) which is representative of the location for the lateral femoral condyle on the surgical plan image.

Figure 8:
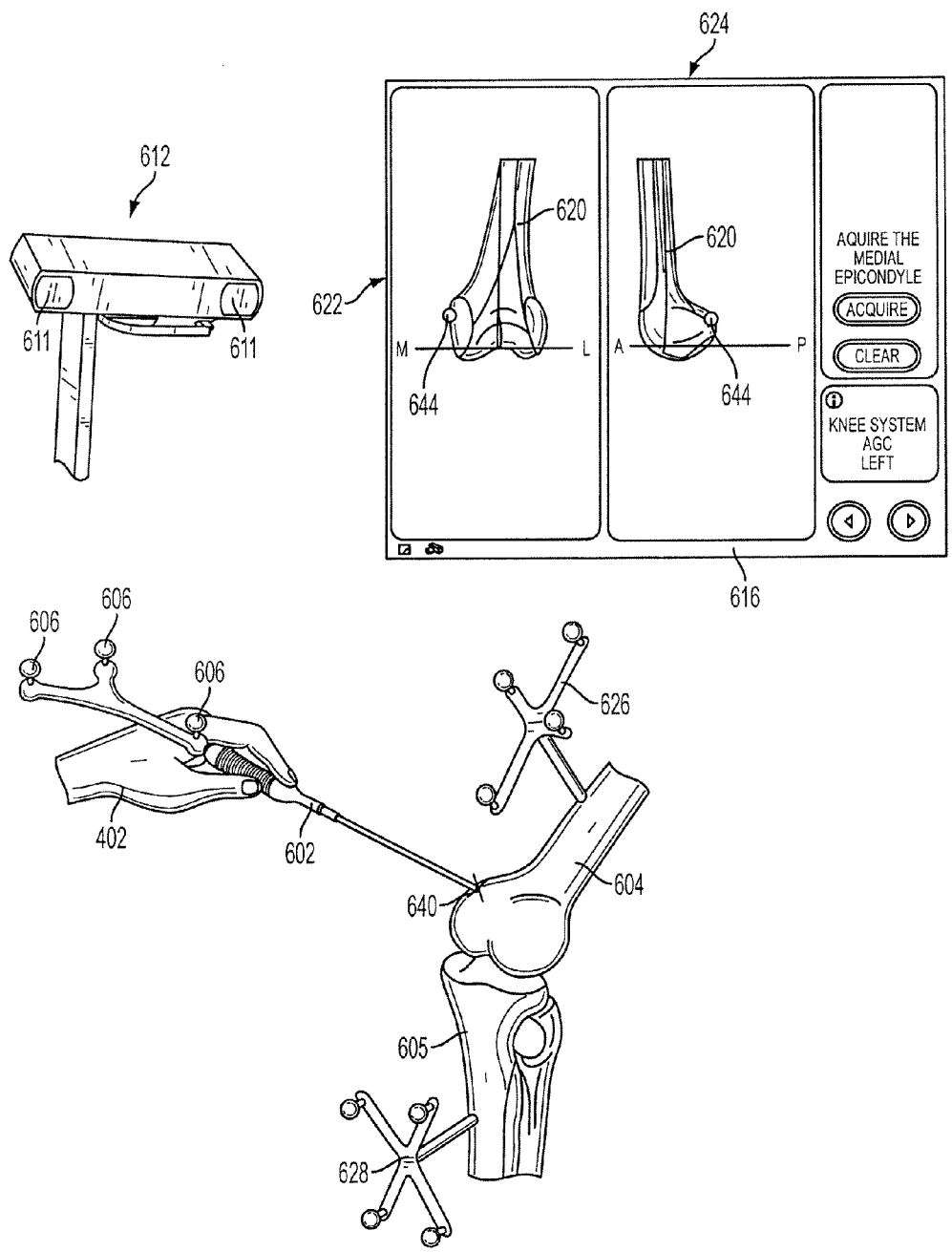
FIG. 8 is a fragmentary perspective view illustrating an exemplary landmark registration for acquiring the medial epicondyle in accordance with the present teachings.
Figure 9:
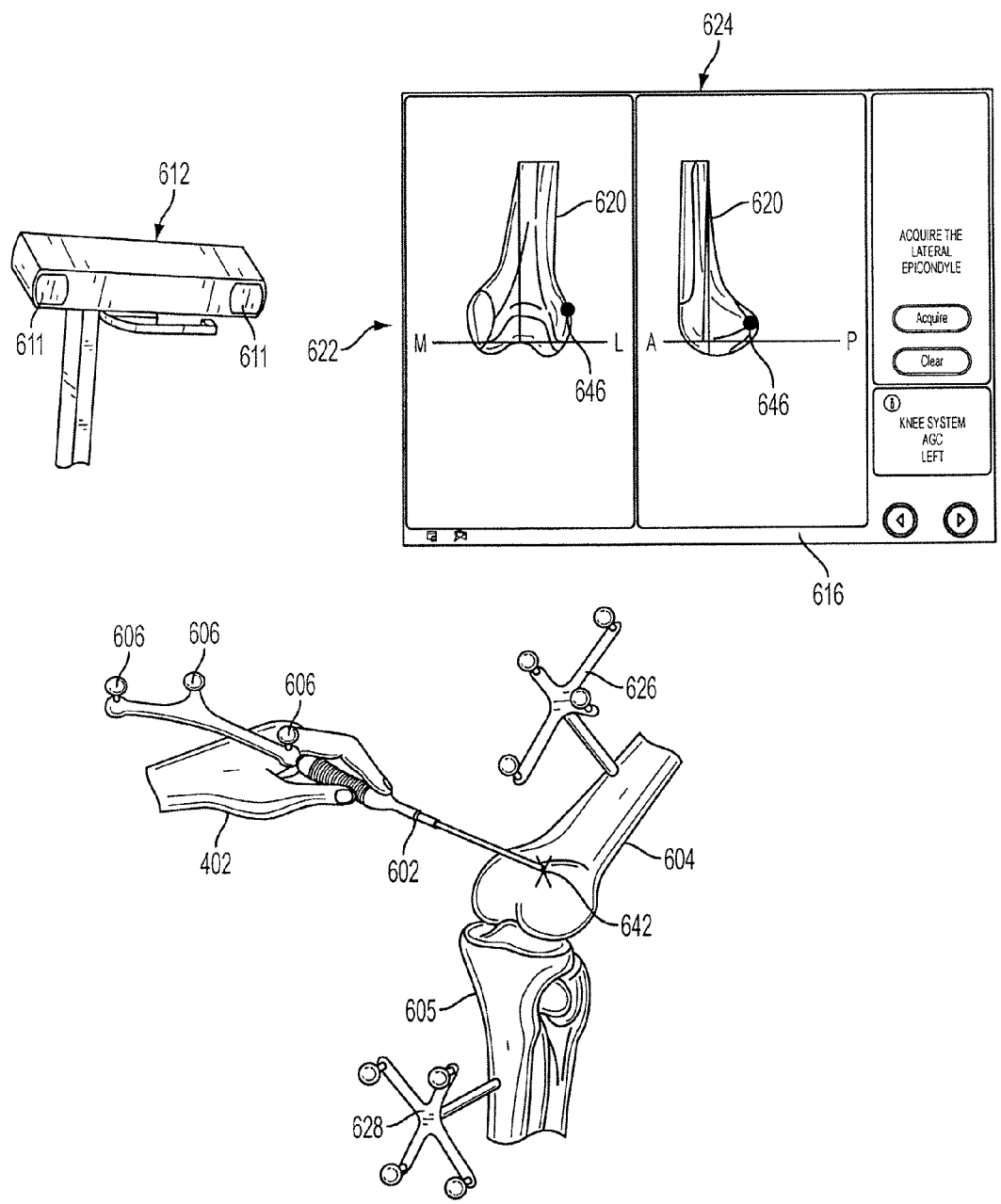
FIG. 9 is a fragmentary perspective view illustrating an exemplary landmark registration for acquiring the lateral epicondyle in accordance with the present teachings.

FIGS. 8 and 9 show the acquisition of the medial and lateral epicondyles, respectively. By acquiring the epicondyles, the transepicondylar axis of the femur can be created to assist with femoral implant rotation. To acquire these positions, surgeon 402 places the tip of surgical probe 602 at the locations believed to correspond to the medial and lateral epicondyles, respectively (shown in FIG. 8 as 640 and in FIG. 9 as 642). After these locations are acquired by the navigation system, points 644 and 646 are shown on surgical plan image 616.

Figure 11:
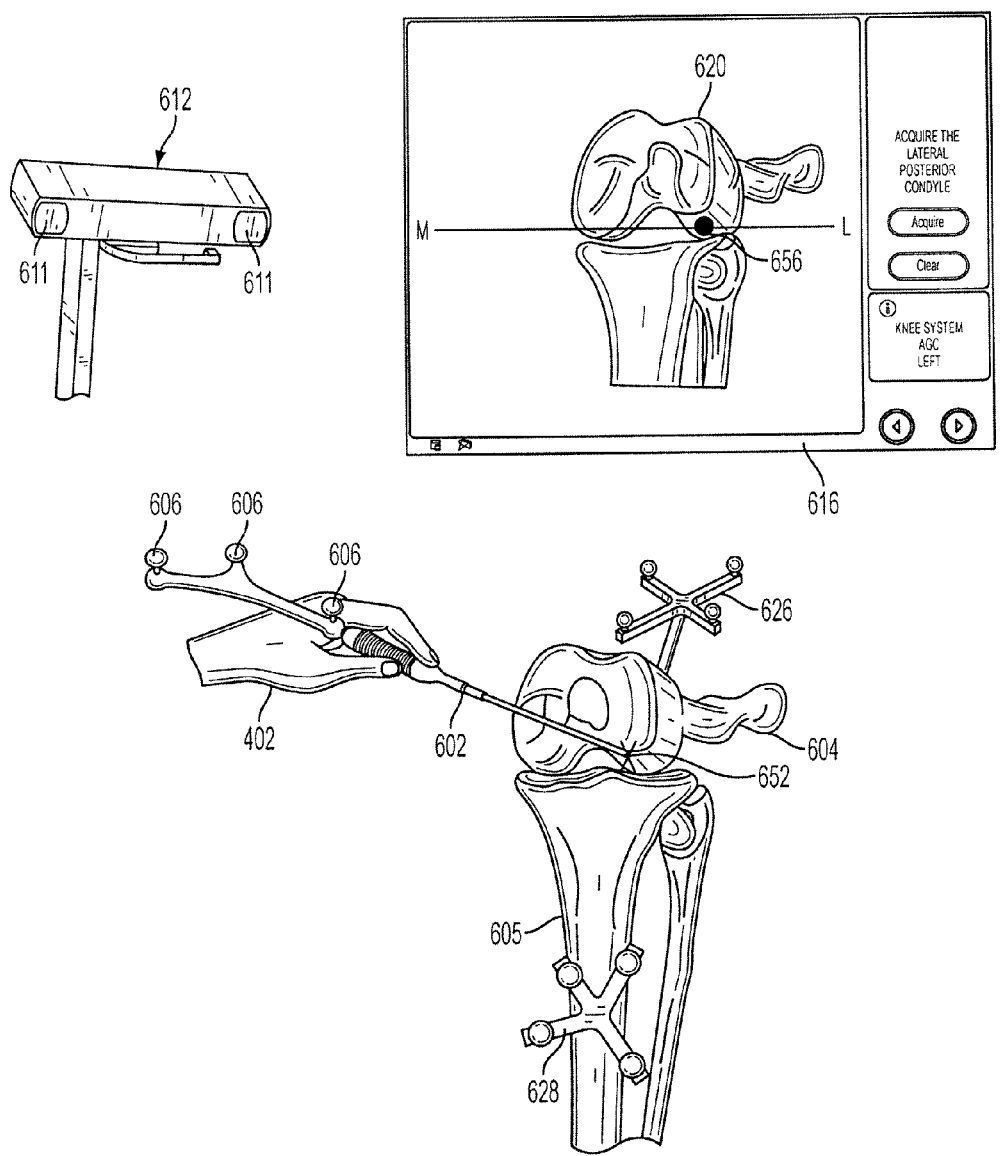
FIG. 11 is a fragmentary perspective view illustrating an exemplary landmark registration for acquiring the lateral posterior condyle in accordance with the present teachings.
Figure 12:
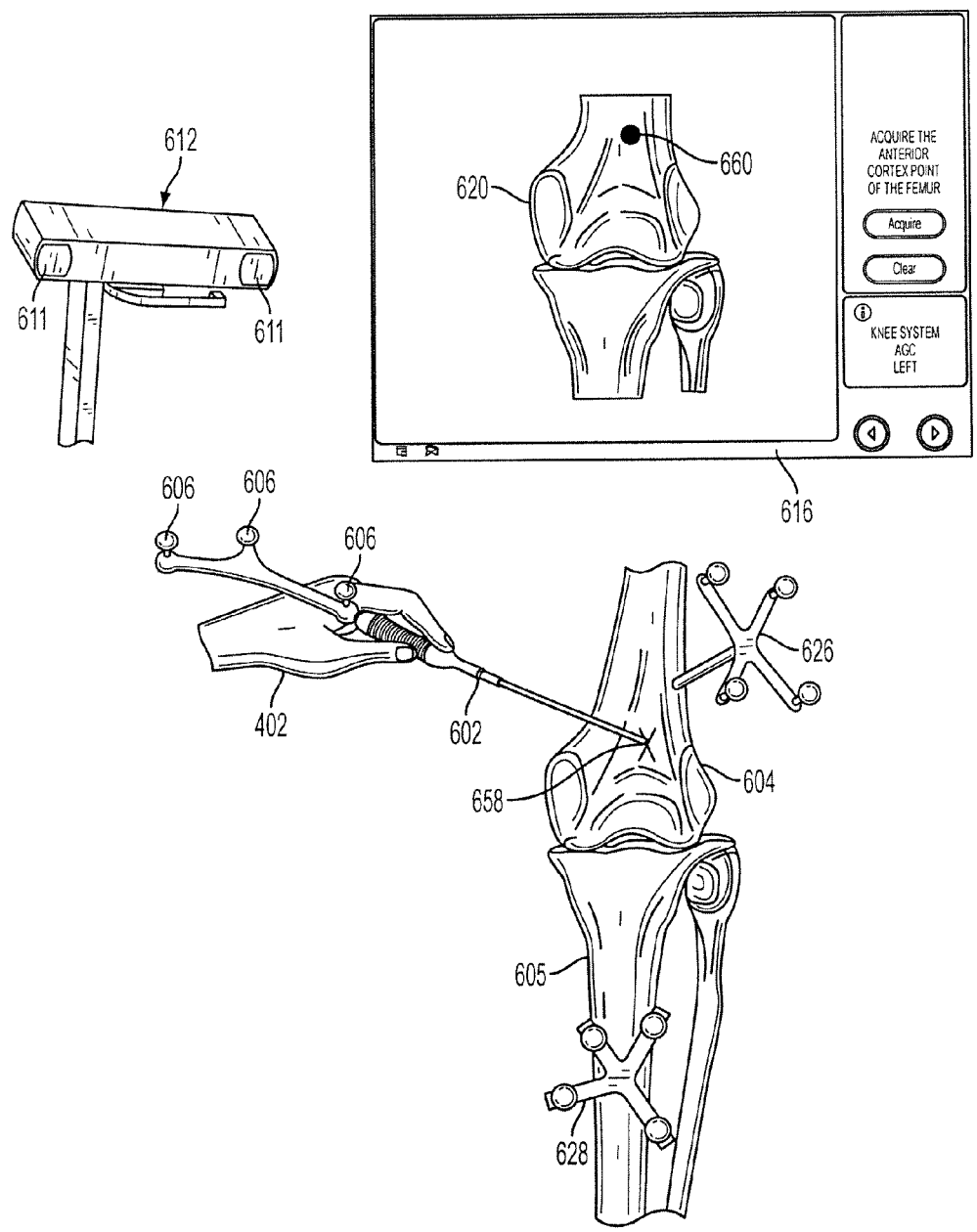
FIG. 12 is a fragmentary perspective view illustrating an exemplary landmark registration for acquiring the anterior cortex point of the femur in accordance with the present teachings.

The femoral landmark registration process concludes with the acquisition of the medial and lateral posterior condyles (FIGS. 10 and 11) and the anterior cortex point of the femur (FIG. 12). The medial and lateral posterior condyles are used to define the posterior-condyle axis, as well as to assist with femoral sizing and rotation. Moreover, the anterior cortex point is also useful for implant sizing.

Figure 10:
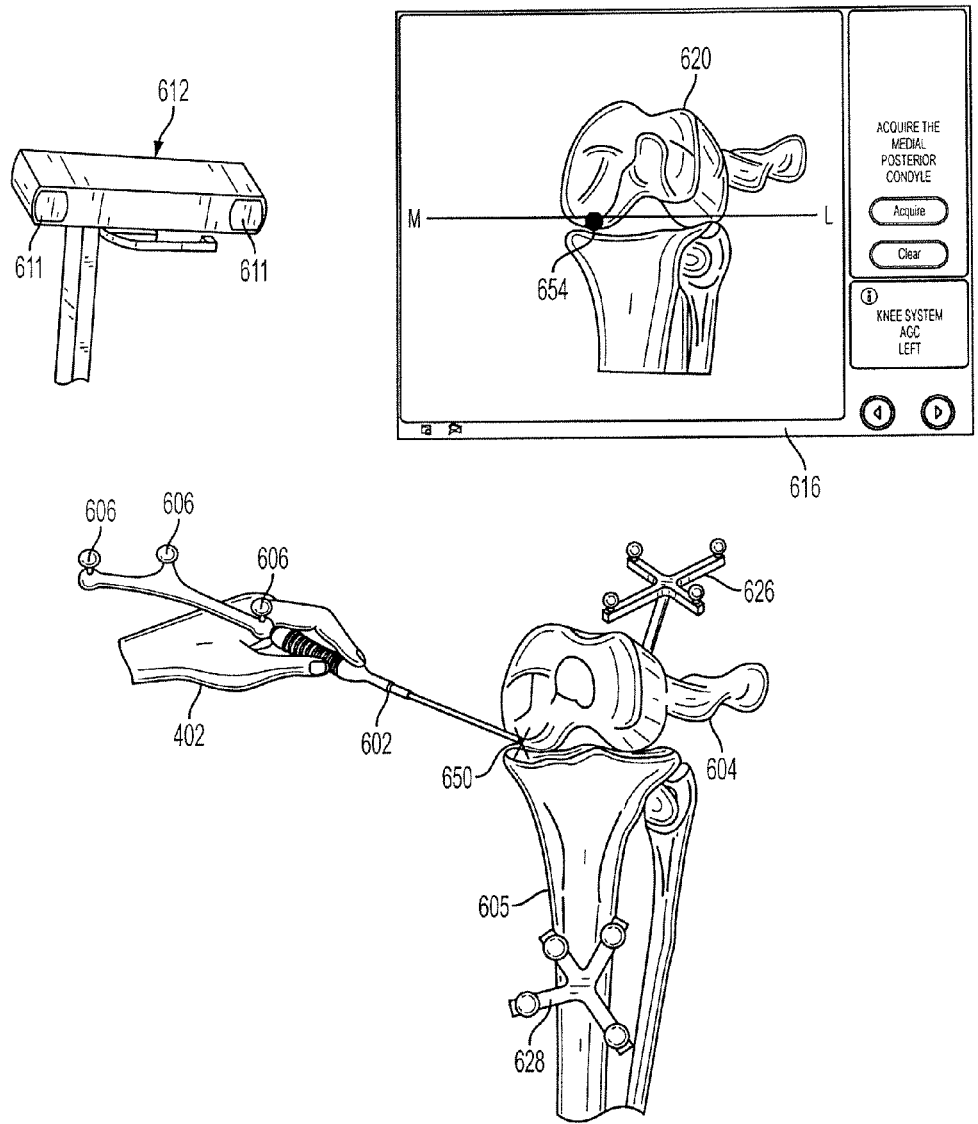
FIG. 10 is a fragmentary perspective view illustrating an exemplary landmark registration for acquiring the medial posterior condyle in accordance with the present teachings.

Referring to FIGS. 10 and 11, surgeon 402 acquires the medial and posterior condyles by respectively placing probe 602 at points 650, 652 on femur 604. Once the probe is detected and registered by the tracking system, surgical plan image 616 displays points 654, 656, which respectively correspond to the medial and posterior condyles. Similarly, in FIG. 12, surgeon 402 acquires the anterior cortex point of femur 604 by placing probe 602 at point 658 on femur 604, which corresponds to point 660 on the surgical plan image.

After all of the femoral landmarks are acquired, the surgeon instructs the system to deform or warp the representative femur model stored within the system's database such that its shape matches the actual bone in at least the positions of the points acquired on the actual bone. More particularly, one or more algorithms associated with the navigation software warp the femoral model so that it changes its representative shape to more physically resemble the patient's actual bone. As explained above, one of skill in the art should understand that the algorithms are configured to change the dimensional appearance of the model so that it is accurate in at least the positions of the points acquired by the navigation system.

Figure 13:
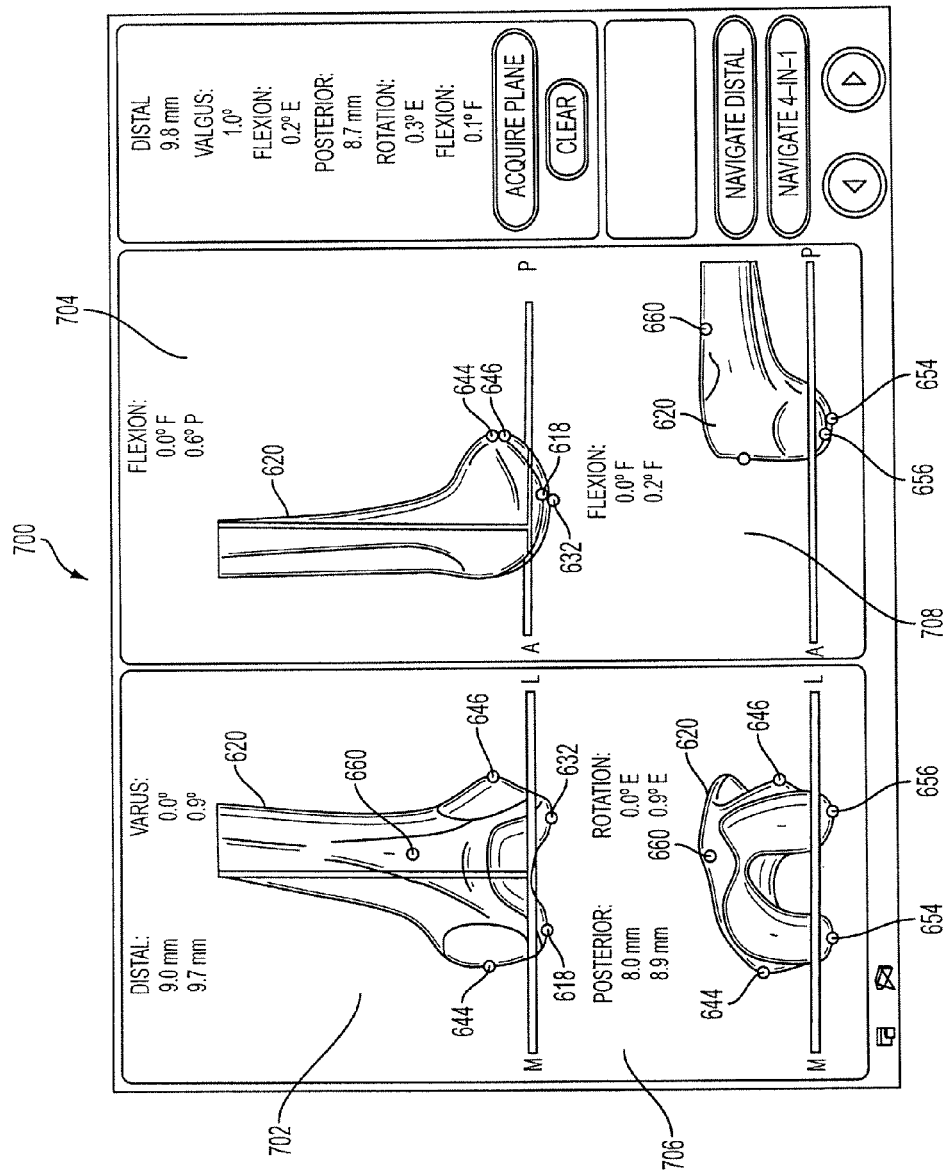
FIGS. 13-16 are exemplary computer navigation screens generally depicting the various femoral landmarks acquired in FIGS. 6a-12.

For instance, in FIG. 13, the seven femoral landmark points acquired in FIGS. 6a-12 (i.e. points 618, 632, 644, 646, 654, 656 and 660) are shown on exemplary computer navigation screen 700, and the location of the displayed femur 604 is accurate at least at positions 614, 630, 640, 642, 650, 652 and 658. The surgeon can use the model as a visual aid and manipulate it intra-operatively to perform the surgery or to gather important surgical information, such as gap analysis data, resection plane details and bone alignment angles. For example, computer navigation screen 700 is split into four sections, 702, 704, 706 and 708 showing femoral model 620 from various perspectives. If the surgeon desires, he can rotate or manipulate femoral model 620 so that he can visually appreciate the general shape and characteristics of the patient's true femur, particularly as the acquired points shown on the various displays remain accurate as they are manipulated by the surgeon.

Figure 14:
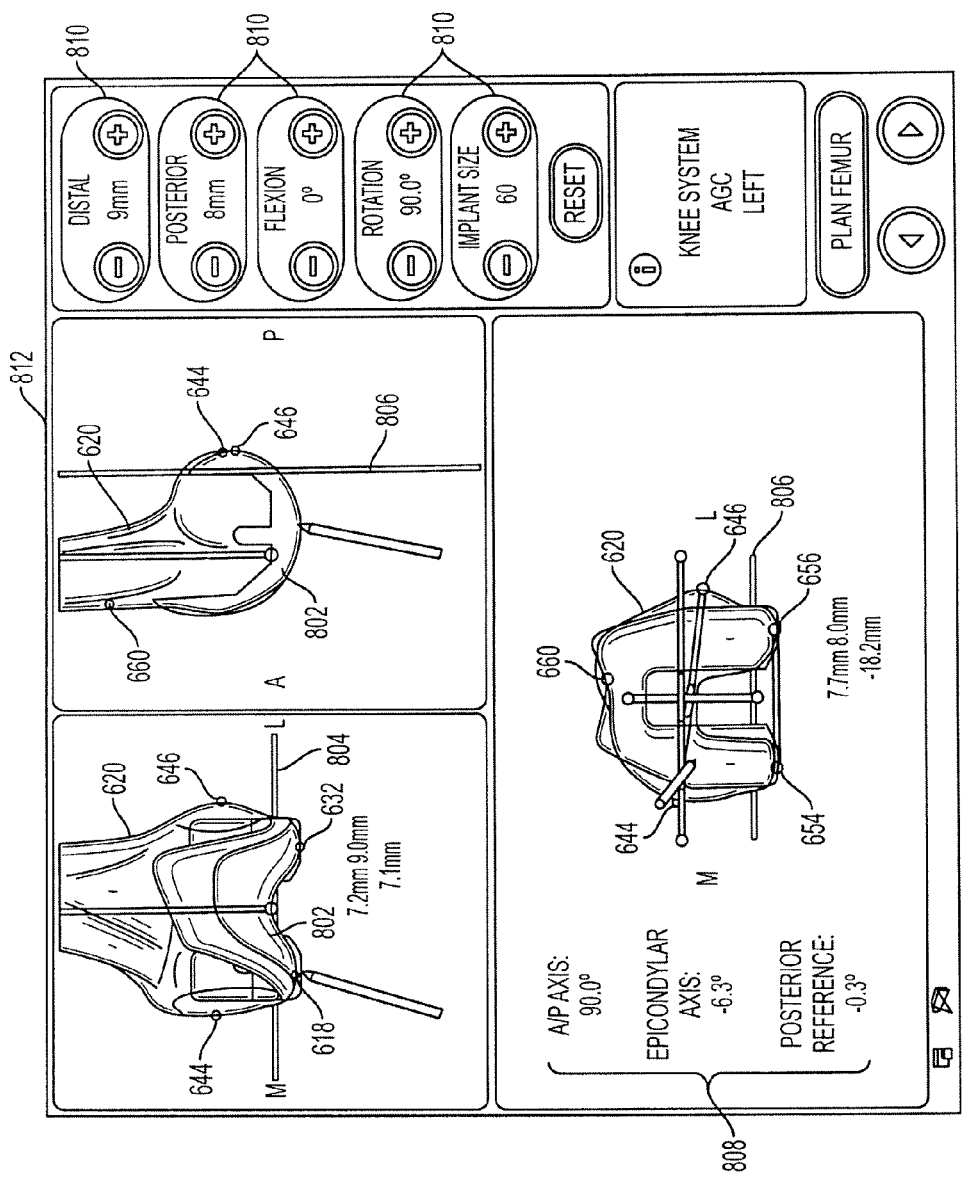

In one exemplary embodiment, according to FIG. 14, femoral model 620 displays the seven femoral landmark points acquired in FIGS. 6a-12 (i.e. points 618, 632, 644, 646, 654, 656 and 660) to conduct femoral component orientation and planning, such as implant sizing and rotation. To accomplish this, an image of the implant 802 to be surgically inserted is displayed on the warped femoral model 620. By utilizing these landmark points, the surgeon can manipulate the orientation of the femoral model to view surgical information such as the planned distal resection plane 804, the planned posterior resection plane 806, as well as various femoral implant rotation data 808. In addition to displaying this information, the surgeon is also able to use buttons 810 on the surgical navigation screen 812 to adjust the femoral implant as needed for planning and sizing purposes. By having this information, the surgeon can intra-operatively adjust the planned femoral orientation data as needed based upon the points acquired during landmark registration and utilize the software to rotate the implant to align it with, for instance, the posterior condylar and transepicondylar axes, as well as manipulate the A/P direction of the femur model. Moreover, the surgeon can also calculate the location of bone cuts and/or the required resection planes needed to conduct the surgery based upon the pre-defined landmark points that have been acquired by the system, as well as navigate the resections. Some resections that can be navigated include, but are not limited to, the tibia proximal cut, femur distal cut, the femur anterior cut, as well as chamfer cuts made by the 4-in-1 resection block.

Figure 15:
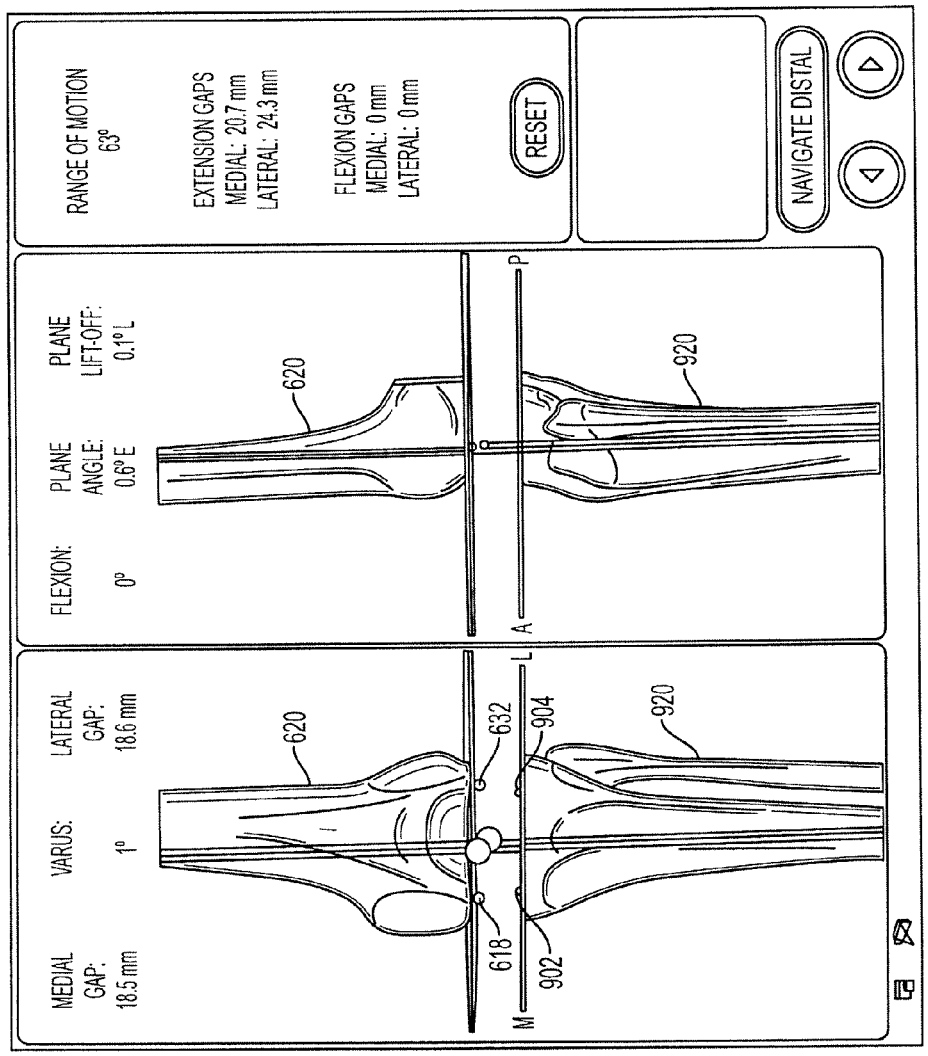
Figure 16:
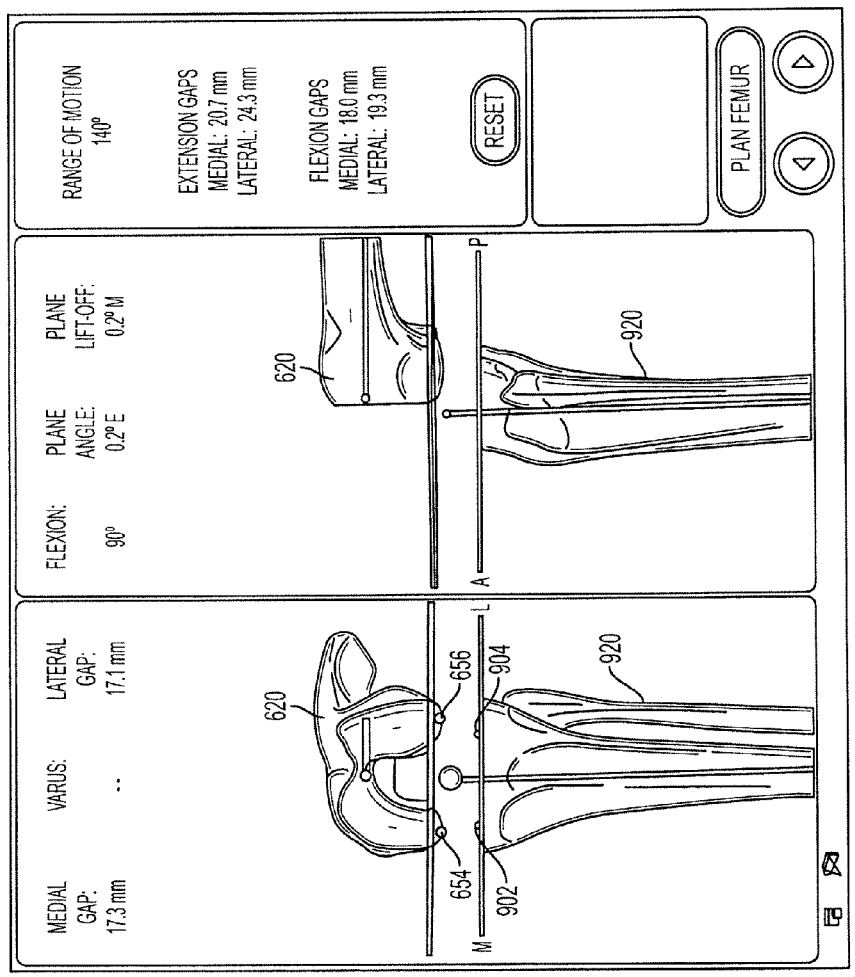

In further exemplary embodiments, and referring to FIGS. 15 and 16, femoral model 620 displays some of the femoral landmark points acquired in FIGS. 6a-12 (i.e. points 618, 632, 644, 646, 654, 656 and 660) for determining the relative distance or gap between medial and lateral compartments of a knee. By acquiring this gap information, the surgeon can balance a joint during reconstructive surgery, as well as determine the level of ligament release required during the surgical procedure. For instance, in a total knee arthroplasty ("TKA") procedure to replace a worn or damaged knee, a significant amount of effort is devoted to ensuring that the resulting knee joint will be balanced. This balancing procedure is referred to as "soft tissue balancing." Balancing may involve releasing the medial or collateral ligaments to correct for a varus or valgus deformity, such that the anatomical axis of the knee is correct when equal forces are applied to both collateral ligaments. A balanced knee joint will demonstrate proper ligament tension through the full range of motion, which provides a natural acting joint and minimizes pain and discomfort. Further, properly balanced ligaments reduce stress, wear and tear on the prosthesis and extend its life.

To perform flexion/extension gap monitoring through a full range of motion during a surgical navigation procedure, the surgeon acquires landmark points on both the medial and lateral condyles of the operative knee. Because the tibia and femur are tracked independent of one another, the distances between both surfaces can be measured at all times. As such, the soft tissues can be monitored before and after the procedure. Turning to a more detailed discussion of this process, the surgeon first chooses at least two distal reference points on the medial and lateral condyles (such as points 618 and 632). Thereafter, the surgeon acquires at least two posterior reference points on the medial and lateral condyles (such as points 654, 656). The surgeon can acquire more points on the femur for better accuracy, however, it should be understood and appreciated that only two points are needed to perform the present gap analysis procedure.

After the points on the femur are acquired, the surgeon proceeds to acquiring points on the tibia. To accomplish this, the surgeon chooses at least one tibial plateau surface point, such as the center of both the medial and lateral plateaus. For instance, in FIGS. 15 and 16, acquired landmark points 902, 904 are shown on warped tibial reference model 920. Similarly to the acquisition of points with the femur, the surgeon can also acquire additional points on the medial and lateral tibial plateau, however, it should be understood and appreciated that only one point is needed to perform the present gap analysis procedure.

By acquiring these points on both the femur and the tibia, the surgeon can perform a gap analysis at any given point through a full range of motion. The flexion/extension gap is measured by software associated with the navigation system as the difference between any corresponding point on the femur with that of an acquired point on the tibia. After determining these gaps, the extension and flexion values can then be compared to verify that the knee is balanced throughout the full range of motion.

The landmark registration and warping processes of the present teachings can also be embodied on a computer readable storage medium. According to these embodiments, the computer readable storage medium stores instructions that, when executed by a computer, cause the surgical navigation system to perform a landmark registration and warping process. The computer readable storage medium can be any medium suitable for storing instruction that can be executed by a computer such as a compact disc (CD), digital video disc (DVD), flash solid-state memory, hard drive disc, floppy disc, and the like.

Advantages and improvements of the processes and methods of the present invention are demonstrated in the following example. This example is illustrative only and is not intended to limit or preclude other embodiments of the invention.

Example

Exemplary Bone Morphine Rules and Algorithms

The following information is provided to illustrate how exemplary warping rules and algorithms can be incorporated into the generic bone modeling processes of the present teachings. It should be understood that these exemplary rules and algorithms are provided for demonstration purposes only, as those skilled in the relevant surgical navigation industry will appreciate that other such mathematical equations and principles may also be used to warp bone models without straying from the teachings of the present invention. As such, the present teachings are not intended to be limited herein.

Rules 1 and 2: Determining Medial Lateral Extreme Points of the Patient

To determine the medial lateral extreme points of a patient, the following factors may be considered: 1) The anterior-posterior (AP) position of the patient's medial sizing point that the surgeon picks becomes the AP position of the patient's extreme point; 2) The lateral position of the patient's extreme point is the lateral position of the model's medial extreme point multiplied by the ratio of:

$$\frac{\text{lateral position of the patient's sizing point}}{\text{lateral position of the model's sizing point}};$$

and 3) For the Superior-Inferior (SI) direction, the ratio of the medial plateau and medial extreme points of the model are determined, such that:

$$\frac{\substack{SI \text{ position of model's extreme point} - \\ SI \text{ position of model's plateau point}}}{\substack{\text{lateral position of model's extreme point} - \\ \text{lateral position of model's plateau point}}} = \frac{\substack{SI \text{ position of patient's extreme point} - \\ SI \text{ position of patient's plateau point}}}{\substack{\text{lateral position of patient's extreme point} - \\ \text{lateral position of patient's plateau point}}}$$

For example, assume that the model's medial extreme points are: (100, 10, 10) for the lateral position, the anterior-posterior position and the superior-inferior position, respectively; the model's medial plateau points are (50, 5, 5); the model's sizing points are (90, 7.5, −30); the patient's sizing points are (100, 15, −20); and the medial plateau points are (100, 5, 5). Then, the AP position of the patient's medial extreme point is 15, and the lateral position of the patient's medial extreme point is 200, i.e., $$\text{lateral position of patient's sizing point } (100) \times$$

$$\frac{\text{lateral position of the patient's sizing point } (15)}{\text{lateral position of the model's sizing point } (7.5)}$$

The superior-inferior position is 15, i.e., the ratio of the model's sizing and extreme point is:

$$\frac{SI \text{ position of model's extreme point } (10) - SI \text{ position of model's plateau point } (5)}{\text{lateral position of model's extreme point } (100) - \text{lateral position of model's plateau point } (50)} = 0.1$$

and the SI position of the patient's medial extreme point is the ratio of the model's sizing point and extreme point (0.1)×(the lateral position of the patient's extreme point (200)−the lateral position of the patient's plateau point (100))+the SI position of the patient's plateau point (5)=15.

After morphing, the medial extreme points (100, 10, 10) of the model are deformed to (200, 15, 15), which are representative of the medial extreme points of the patient.

Rule 3: Determining the Spine Points of the Tibia

To determine the spinal points of the tibia, the following may be considered: 1) the concave shape of medial/lateral condyle and 2) the slope between the spinal points. With respect to the concave shape of the medial/lateral condyle, the medial/lateral condyles of the tibia bone model are assumed to have a concave shape. The spine point of the model is adjusted to make this assumption true. The linear equation connecting the extreme point and plateau of the model is calculated using equations presented below in the calculation section. If the spine point of the model (in the superior-inferior direction) is below the line, then the spine point is moved up to above the line so that the condyle has a concave shape.

Next, the slope between the two spine points is determined. In particular, it is determined that the slope of the line in the superior-inferior (SI) direction, connecting two spine points of the patient should be the same as that of the model after bone morphing to keep the resemblance of a human tibia. The position of the patient's spine points are determined as follows:

1) Lateral position of the patient's spine point is determined as:

lateral position of patient's plateau×

$$\frac{\text{lateral position of the model's spine point}}{\text{lateral position of the model's plateau}};$$

2) The SI position of the patient's (medial/lateral) spine point is:

((SI position of model's (medial/lateral) spine point−SI position of model's knee center) scale ratio)−SI position of model's (medial/lateral) spine point, where "scale ratio" is:

$$\frac{(SI \text{ position of patient's medial plateau} - SI \text{ position of patient's knee center})}{(SI \text{ position of model's medial plateau} - SI \text{ position of model's knee center})} \text{ if}$$

$$\frac{(SI \text{ position of patient's medial plateau} - SI \text{ position of patient's knee center})}{(SI \text{ position of model's medial plateau} - SI \text{ position of model's knee center})} \text{ is larger than}$$

-continued $$\frac{(SI \text{ position of patient's lateral plateau} - SI \text{ position of patient's knee center})}{(SI \text{ position of model's medial plateau} - SI \text{ position of model's knee center})} \text{ or}$$

$$\frac{(SI \text{ position of patient's lateral plateau} - SI \text{ position of patient's knee center})}{(SI \text{ position of model's lateral plateau} - SI \text{ position of model's knee center})} \text{ if}$$

$$\frac{(SI \text{ position of patient's lateral plateau} - SI \text{ position of patient's knee center})}{(SI \text{ position of model's lateral plateau} - SI \text{ position of model's knee center})} \text{ is larger than}$$

$$\frac{(SI \text{ position of patient's medial plateau} - SI \text{ position of patient's knee center})}{(SI \text{ position of model's medial plateau} - SI \text{ position of model's knee center})}$$

For example, assume that: the model's medial plateau is (50, 5, 5) for its lateral position, anterior-posterior position and superior-inferior position, respectively; the model's medial spine points are (10, 5, 10); the model's ankle points are (0, 0, −500); the model's lateral plateau is (−40, 7, 7); the model's lateral spine points are (−8, 3, 9); the patient's medial plateau points are (70, 10, 10); the patient's lateral plateau points are (−60, 5, 5); and the patient's ankle points are (0, 0, −505). Then, the lateral position of the patient's medial spine point is:

$$70 \times \left(\frac{10}{50}\right) = 14,$$

and the lateral position for the patient's lateral spine point is:

$$-60 \times \left(\frac{-8}{-40}\right) = -12.$$

The scale ratio is 1.0198 ((10−(−505))/(5−(−500)) for the medial side, and, 1.00592 ((5−(−505)/(7−(−500)) for the lateral side. Then, the SI position of the patient's medial spine point is: ((10−(−500)×1.0198)−(−500)=20.098, and the SI position of the patient's lateral spine point is: ((9−(−500)×1.00592)−(−500)=12.013.

After morphing, the medial spine points (10, 5, 10) of the model are deformed to (14, not used, 20.098), medial spine points of the patient, and lateral spine points (−8, 3, 9) to (−12, not used, 12.013), lateral spine points of the patient.

Calculations: It should be understood and appreciated herein that for calculation purposes, two points uniquely determine a line. (see also, the paper entitled, "Equation of a Circle from 3 Points (2 dimensions)" by Paul Bourke: located at website: http://local.wasp.uwa.edu.au/~pbourke/geometry/circlefrom3/, the disclosure of which is incorporated by reference herein). As such, if the points $(x_1, y_1)$ and $(x_2, y_2)$ are vertical, then the equation $x=x_1$ can be used. If the two points are not vertical, however, $y=mx+b$, can be used, such that:

$$m = \left(\frac{y2 - y1}{x2 - x1}\right) \text{ and } b = \left(\frac{x2y1 - x1y2}{x2 - x1}\right).$$

While exemplary embodiments incorporating the principles of the present teachings have been disclosed hereinabove, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain and which fall within the limits of the appended claims.

What is claimed is:

1. A method of modeling a bone during a surgical navigation procedure, comprising:
   providing a tracking system and a modeling instrument detectable by the tracking system;
   acquiring up to nine predefined points from a bone with the modeling instrument, the acquired points being used to generate a representative model of the bone;
   associating the representative model of the bone with a reference bone model from a computer database associated with the tracking system;
   warping the reference bone model to at least coincide with the representative model of the bone at the locations of the acquired predefined points;
   displaying a three-dimensional and manipulatable image of the warped reference bone model, the image showing the acquired predefined points;
   intra-operatively manipulating the image of the warped reference bone model to calculate a bone cut or to determine surgical information for performing the surgical procedure, the surgical information including gap analysis data, resection plane details and bone alignment angles; and
   wherein the displayed warped reference bone model accurately represents the location of the patient's bone in real time in at least the locations of the acquired predefined points.

2. The method of claim 1, wherein up to seven predefined points are acquired from the bone with the modeling instrument.

3. The method of claim 1, wherein calculating a bone cut comprises analyzing the predefined points on the warped reference bone model.

4. The method of claim 1, further comprising displaying an image of an implant on the warped reference bone model.

5. The method of claim 1, further comprising displaying an image of a cutting location on the warped reference bone model.

6. The method of claim 1, wherein the bone being modeled comprises a femur.

7. The method of claim 1, wherein the bone being modeled comprises a tibia.

8. The method of claim 1, wherein at least one of the predefined points is a landmark selected from the group consisting of a femoral head landmark, a central knee landmark, a medial femoral condyle landmark, a lateral femoral condyle landmark, a medial epicondyle landmark, a lateral epicondyle landmark, a medial posterior condyle landmark, a lateral posterior condyle landmark and an anterior cortex point landmark.

9. An image guided surgery system, comprising:
   a tracking system having a measurement field;
   a modeling instrument detectable by the tracking system when exposed to the measurement field;
   means for generating a representative model of a bone while the modeling instrument acquires up to nine predefined points from the bone;
   means for associating the representative model of the bone with a reference bone model contained within a computer database that is associated with the tracking system;
   means for warping the reference bone model to at least coincide with the representative bone model at the locations of the acquired predefined points;
   means for displaying a three-dimensional and manipulatable image of the warped reference bone model, the image accurately showing the location of the patient's bone in real time in at least the locations of the acquired predefined points; and
   means for intra-operatively manipulating the image of the warped reference bone model to calculate a bone cut or to determine surgical information for performing a surgical procedure, the surgical information including gap analysis data, resection plane details and bone alignment angles.

10. The system of claim 9, further comprising a means for displaying an image of an implant on the warped reference bone model.

11. The system of claim 9, further comprising a means for displaying an image of a cutting location on the warped reference bone model.

12. The system of claim 9, wherein up to seven predefined points are acquired from the bone with the modeling instrument.

13. The method of claim 1, wherein from seven to nine predefined points are acquired from the bone with the modeling instrument.

14. The system of claim 9, wherein from seven to nine predefined points are acquired from the bone with the modeling instrument.

* * * * *